US011773378B2

(12) United States Patent
Lynch et al.

(10) Patent No.: US 11,773,378 B2
(45) Date of Patent: *Oct. 3, 2023

(54) IN VIVO PROTEIN N-ACYLATION

(71) Applicant: Duke University, Durham, NC (US)

(72) Inventors: Michael David Lynch, Durham, NC (US); Romel Menacho Melgar, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 111 days.

This patent is subject to a terminal disclaimer.

(21) Appl. No.: 17/343,156

(22) Filed: Jun. 9, 2021

(65) Prior Publication Data
US 2021/0332335 A1 Oct. 28, 2021

Related U.S. Application Data

(62) Division of application No. 16/488,973, filed as application No. PCT/US2018/020004 on Feb. 27, 2018, now Pat. No. 11,180,739.

(60) Provisional application No. 62/463,811, filed on Feb. 27, 2017.

(51) Int. Cl.
| | |
|---|---|
| C12N 9/10 | (2006.01) |
| C07K 7/06 | (2006.01) |
| C07K 14/50 | (2006.01) |
| C07K 14/505 | (2006.01) |
| C07K 14/535 | (2006.01) |
| C07K 14/555 | (2006.01) |
| C07K 14/575 | (2006.01) |
| C07K 14/59 | (2006.01) |
| C07K 14/605 | (2006.01) |
| C07K 14/61 | (2006.01) |
| C07K 14/62 | (2006.01) |
| C07K 14/755 | (2006.01) |
| C12N 9/16 | (2006.01) |
| C12N 9/64 | (2006.01) |
| C12N 9/82 | (2006.01) |
| C12P 21/00 | (2006.01) |

(52) U.S. Cl.
CPC ............. *C12N 9/1029* (2013.01); *C07K 7/06* (2013.01); *C07K 14/50* (2013.01); *C07K 14/505* (2013.01); *C07K 14/535* (2013.01); *C07K 14/555* (2013.01); *C07K 14/575* (2013.01); *C07K 14/57527* (2013.01); *C07K 14/57545* (2013.01); *C07K 14/59* (2013.01); *C07K 14/605* (2013.01); *C07K 14/61* (2013.01); *C07K 14/62* (2013.01); *C07K 14/755* (2013.01); *C12N 9/16* (2013.01); *C12N 9/644* (2013.01); *C12N 9/82* (2013.01); *C12P 21/00* (2013.01); *C12Y 203/01016* (2013.01); *C12Y 203/01097* (2013.01); *C12Y 301/0202* (2013.01); *C12Y 304/21022* (2013.01); *C12Y 305/01001* (2013.01); *C07K 2319/20* (2013.01); *C07K 2319/50* (2013.01)

(58) Field of Classification Search
CPC ........ C12N 9/1029; C07K 7/06; C07K 14/50; C07K 14/505; C07K 14/555; C07K 14/575; C07K 14/57527; C07K 14/57475; C07K 14/59; C07K 14/605; C07K 14/61; C07K 14/62; C07K 14/755
See application file for complete search history.

(56) References Cited

U.S. PATENT DOCUMENTS

| | | | |
|---|---|---|---|
| 5,436,138 A | 7/1995 | Duronio et al. | |
| 5,631,347 A | 5/1997 | Baker et al. | |
| 6,444,641 B1 | 9/2002 | Flora | |
| 11,180,739 B2 * | 11/2021 | Lynch | ..................... C12N 9/16 |
| 2004/0014764 A1 | 1/2004 | Smith et al. | |
| 2005/0118665 A1 | 6/2005 | Zhou et al. | |
| 2008/0286749 A1 | 11/2008 | Fox et al. | |
| 2012/0184465 A1 | 7/2012 | Picataggio et al. | |
| 2012/0283171 A1 * | 11/2012 | Putman | ................... A61P 31/00 514/11.3 |
| 2013/0224810 A1 | 8/2013 | Seshadri et al. | |
| 2016/0272950 A1 | 9/2016 | Corthals et al. | |
| 2016/0340700 A1 | 11/2016 | Liao et al. | |

FOREIGN PATENT DOCUMENTS

| | | |
|---|---|---|
| WO | 0112817 A1 | 2/2001 |

OTHER PUBLICATIONS

Puig et al., "The tandem affinity purification (TAP) method: a general procedure of protein complex purification", Methods, May 25, 2002, vBol. 24. pp. 218-229.

(Continued)

*Primary Examiner* — Ganapathirama Raghu
(74) *Attorney, Agent, or Firm* — BENESCH, FRIEDLANDER, COPLAN & ARONOFF LLP

(57) ABSTRACT

Described are a genetically modified microorganism and corresponding methods and products. The genetically modified microorganism may include a first gene that encodes an acyl transferase and a second gene that encodes a peptide or protein. One or both of the first and second gene may be heterologous. The genetically modified microorganism may include a modified acyl-CoA biosynthetic pathway configured for one or more of: inducible biosynthesis of an acyl-CoA and over-accumulation of the acyl-CoA. The genetically modified microorganism may be effective upon fermentation to cause acylation of the peptide or protein by the acyl transferase using the acyl-CoA to provide a N-acylated peptide or protein product.

14 Claims, 4 Drawing Sheets
Specification includes a Sequence Listing.

(56) References Cited

OTHER PUBLICATIONS

International Search Report and Written Opinion Issued in corresponding PCT application No. PCT/2018/020004, dated Jul. 5, 2018.
Extended European Search Report issued in European patent application No. 18758361.2, dated Sep. 11, 2020.
L. J. Knoll, et al., "Use of *Escherichia coli* strains containing fad mutations plus a triple plasmid expression system to study the import of myristate, its activation by *Saccharomyces cerevisiae* acyl-CoA synthetase, and its unilzation by S. cerevisiae myristoyl-CoA; protein N-myristoyltransferase", Journal of Biological Chemistry, vol. 268. No. 6, Feb. 25, 1993, pp. 4281-4290.
Broun et al., "Catalytic plasticity of fatty acid modification enzymes underlying chemical diversity of plant lipids", Science, 1998, vol. 282, 1315-1317.
Chica et al., Semi-rational approaches to engineering enzyme activity: combining the benefits of directed evolution and rational design, Curr. Opi. Biotechnol. 2005, vol. 16: 378384.
Devos et al., "Practical limits of function prediction", Problems: Structure, Function and Genetics, 2000, vol. 41: 98-107.
Gao et al., "Temporal Hierarchy of Gene Expression Mediated by Transcription Factor Binding Affinity and Activation Dynamics", mBIO, 2015, vol. 6(3), e00686-15, pp. 1-10.
Guckes et al., "Signaling by two-component system noncognate partners promotes intrinsic tolerance to polymyxin B in uropathogenic *Escherichia coli*", Sci. Signal., 2017, vol. 10, eaag1175: pp. 1-9.
Kisselev, L., "Polypeptide release factors in prokaryotes and eurkaryotes; same function, different structure", Structure, 2002, vol. 10: 8-9.
Kuo et al., SUMO as a Solubility Tand in Vivo Cleavage of SUMO Fusion Proteins with Ulp1. Prot. Affinity Tags: Methods and Protocols, Methods in Mol. Biol., Chapter 6, 2014, pp. 71-80.

Kumar et al., "An improved method and cost effective strategy for soluable expression and purification of human N-myristoyltransferase 1 in *E. coli*", Mol Cell Biol., 2014, vol. 392: 175-186.
Resh, M.D., "Fatty acylation of proteins: new insights into membrane targeting of myristoylated and palmitoylated proteins", Biochim. Biophys. Acta., 1451, 1999: 1-16.
Rudnick et al., "Myristoylcoa: Protein N-Myristoyltransferase", Adv. Enzymol. Mol. Biol., 1993, vol. 67, 375-430.
Seffernick et al., "Melamine deaminase and Atrazine chlorohydrolase: 98 percent identical but functionally different", J. Bachteriol., 2001, vol. 183 (8), 2405-2410.
Sen et al., "Developments in directed evolution for enzyme functions", Appl. Biochem. Biotechnol., 2007, vol. 143, 212-223.
Whisstock et al., "Prediction of protein function from protein sequence", Q. Rev. Biophysics., 2003, vol. 36(3), 307-340.
Wishart et al., "A single mutation converts a novel phosphotyrosine binding domain into a dual-specificity phosphatase", J. Biol. Chem., 1995, vol. 270(45), 26782-26785.
Soupene et al., "Association of NMT2 with the acyl-CoA carrier ACBD6 protects the N-myristoltransferase reaction from palmityol-CoA", J. Lipid Res., 2016, vol. 57, 288-297.
Witkowski et al., "Conversion of b-ketoacyl to a Malonyl Decaboxylase by replacement of the active cysteine with glutamine", Biochemistry, 1999, vol. 38, 11643-11650.
Guo et al., "Metabolic engineering of *Escherichia coli* for producation of fatty acid short-chain esters through combination of the fatty acit and 2-keto acid pathways", Metabol. Eng., 2014, vol. 22: 69-75.
Kumar et al., "N-Terminal Region of the Catalytic Domain of Human N-Myrstoyltransferase 1 Acts as an Inhibitory Module", PLOS ONE DOI:10.1371/journal.pone.0127661 May 22, 2015, pp. 1-20.

\* cited by examiner

IN VIVO PROTEIN N-ACYLATION

This application is a divisional application of U.S. application Ser. No. 16/488,973, filed Aug. 27, 2019, which is a National Stage Entry of PCT/US18/20004, filed Feb. 27, 2018 which claims priority to U.S. Provisional Pat. App. No. 62/463,811, filed on Feb. 27, 2017, all of which are incorporated by reference herein in its entirety.

BACKGROUND

The use of biologics to treat a myriad of conditions is on the rise, with an ever increasing percentage of the population benefiting from these drugs. The use of candidate proteins in effective clinical therapies, however, may often benefit from modification. For example, modification with polyethylene glycol chains (PEGylation) may increase the stability of biologics. However PEGylation may result in a heterogeneous population of molecules due to nonspecific chemistry, which may complicate the study, approval, and replication of these drugs. Moreover, PEGylation may not be effective in reducing immunogenicity and may result in the production of anti-PEG antibodies, leading to the loss of therapeutic efficacy, increased adverse reactions, and the like.

As an alternative to PEGylation, Lipidation, e.g., via N-acylation may enhance the binding of a desired protein to serum albumin or other carrier proteins, increasing drug half-life. Methods for the chemical synthesis of lipidated proteins have been developed, but these may use multiple steps, may have low specificity, may result in low yields, and the like. Biological synthesis of lipidated proteins has been demonstrated, e.g., myristoylation of proteins in E. coli. However, these approaches used the native ability of E. coli to uptake and activate free fatty acids from culture medium Such approaches used addition of detergent solubilized fatty acids to the medium, and also the use of rich media, as fatty acid uptake and activation is known to be repressed in commercially relevant minimal media. Accordingly, such known methods may be low yield, laborious, expensive, and of low utility for production at larger scales.

The present application appreciates that modification of proteins and peptides, e.g., for production of therapeutics, may be a challenging endeavor.

SUMMARY

In one embodiment, a genetically modified microorganism is provided. The genetically modified microorganism may include a first gene that encodes an acyl transferase. The genetically modified microorganism may include a second gene that encodes a peptide or protein. One or both of the first and second gene may be heterologous with respect to a corresponding native microorganism. The genetically modified microorganism may include a modified acyl-CoA biosynthetic pathway. Compared to a native acyl-CoA biosynthetic pathway in the native microorganism, the modified acyl-CoA biosynthetic pathway may be configured for one or more of: inducible biosynthesis of an acyl-CoA and over-accumulation of the acyl-CoA. The genetically modified microorganism may be effective upon fermentation to cause acylation of the peptide or protein by the acyl transferase using the acyl-CoA to provide a N-acylated peptide or protein product.

In another embodiment, a method of in vivo acylation of a target peptide or protein in a genetically modified microorganism is provided. The method may include expressing an acyl transferase encoded by a first gene. The method may include expressing a peptide or protein encoded by a second gene. One or both of the first and second gene may be heterologous compared to a corresponding native microorganism. The method may include producing an acyl-CoA using a modified acyl-CoA biosynthetic pathway. The method may include fermenting the microorganism under conditions effective to cause acylation of the peptide or protein by the acyl transferase using the acyl-CoA to provide a N-acylated peptide or protein product.

In one embodiment, a N-acylated therapeutic peptide or protein is provided. The N-acylated therapeutic peptide or protein may be produced by fermentation of any aspect of the genetically modified microorganism as described herein. The N-acylated therapeutic peptide or protein may be produced by any of the methods described herein.

In another embodiment, a gene or plasmid construct is provided. The gene or plasmid construct may include any gene or oligonucleotide described herein, or any gene or oligonucleotide for any protein, peptide, enzyme, tag, or other expression product described herein. The gene or plasmid construct may include, for example, one or more of: SEQ ID NO: 28, 30, 31, 32, 33, and 36.

```
BRIEF DESCRIPTION OF THE SEQUENCES
SEQ ID NO: 1 is Primer tetA F.
atcaaaggga aaactgtcca tatgc SEQ ID NO: 2 is Primer sac B R:
atcaaaggga aaactgtcca tatgc SEQ ID NO: 3 is Primer arsB-tetA-F:
caaatgaata gccaactcaa aattcacacc tattaccttc ctctgcactt cctaattttt gttgacactc tatc SEQ ID NO: 4 is Primer arsB-sacB-R:
aaataaagcg cacttttcta acaacctgtg gggggatat cgccgctatc aaagggaaaa ctgtccatat gc SEQ ID NO: 5 is Primer ompT_tetA:
agatataaaa aatacatatt caatcattaa aacgattgaa tggagaactt tttcctaatt tttgttgaca ctctatc SEQ ID NO: 6 is Primer ompT_sacB:
gaaatggcta gttattcccc ggggcgattt tcacctcggg gaaattttag ttgatcaaag ggaaaactgt ccatatgc SEQ ID NO: 7 is Primer500up:
aacggataag acgggcataa at SEQ ID NO: 8 is Primer500dn:
agattaaggg atgaaggaac gtc
```

SEQ ID NO: 9 is Primer500up:
atttccgtgg acaactggtt a

SEQ ID NO: 10 is Primer fadD 500dn:
ggacggcttc acacaaag

SEQ ID NO: 11 is Primer fadD_seq_F:
aactgaataa ttgcttgttt tt

SEQ ID NO: 12 is Primer fadD_seq_R:
gctcaaacat atctaccaga ga

SEQ ID NO: 13 is Primer fadE_500up:
tgactaacg tcagaaatag c

SEQ ID NO: 14 is Primer fadE 500dn:
cgggaggaat gatgtttaag

SEQ ID NO: 15 is Primer fadE_seq_F:
atgtttttac atccactaca ace

SEQ ID NO: 16 is Primer fadE_seq_R.:
atccggatgg ctttaatttt

SEQ ID NO: 17 is Primer fadE mid:
tgggtacgt ttgaccacc

SEQ ID NO: 18 is Primer removeSUMO F:
gggaacgcag cagct

SEQ ID NO: 19 is Primer removeSUMO R:
cattatatcc tccttaatag tattttataa aagttaaac SEQ ID NO: 20 is Primer SL1:
cagtccagtt acgctggagt c SEQ ID NO: 21 is Primer SR2:
ggtcaggtat gatttaaatg gtcagt SEQ ID NO: 22 is Primer pCDF_piece1_F.:
gacgaattct ctagatatcg c SEQ ID NO: 23 is Primer CDF_piece1_R:
gcaggtatct tcgagcca SEQ ID NO: 24 is Primer pCDF_piece2_F:
tggctcgaag atacctgc SEQ ID NO: 25 is Primer pCDF_piece2_R:
ggaaaccgtt gtggtctc SEQ ID NO: 26 is Primer Δ80_hNMT-1_F:
aactcgttgc ctgctgag SEQ ID NO: 27 is Primer Δ80_hNMT-1_R:
gtgatggtga tggtgatgca t SEQ ID NO: 28 is vector ΔarsB::ugpBp-6xHIS-ulpl (383-1093 is ulpl. 203-285 ugpB):
ccaggcatca aataaaacga aaggctcagt cgaaagactg ggcctttcgt tttatctgtt gtttgtcggt gaacgctctc tactagagtc acactggctc accttcgggt gggcctttct gcgtttatac acagctaaca ccacgtcgtc cctatctgct gccctaggtc tatgagtggt tgctggataa ctctttctga caccttacta tcttacaaat gtaacaaaaa agttatttt ctgtaattcg agcatgtcat gttaccccgc gagcataaaa cgcgtatatt cagggagacc acaacggttt ccctctacaa ataattttgt ttaactttga attcaaaaga tctggtacca cctttaagaa ggagatatac atatgcgggg ttctcatcac catcatcacc atggtctggt tccgcgtgga tcccttgttc ctgaattaaa tgaaaagac gatgaccaag tacaaaaagc tttggcatct agagaaaata ctcagttaat gaatagagat aatatagaga taacagtacg tgatttaag accttggcac cacgaagatg gctaaatgac actatcattg attttttt gaaatacatt gaaaatcta cccctaatac agtggcgttt aattcgtttt tctataccaa tttatcagaa aggggttatc aaggcgtccg gaggtggatg aagagaaaga agacacaaat tgataaactt gataaatct ttacaccaat aaatttgaac caatcccact gggcgttggg cataattgat ttaaaaaga aaactatagg ttacgtagat tcattatcga atggtccaaa tgctatgagt ttcgctatac tgactgactt gcaaaaatat gttatggagg aaagtaagca tacaatagga gaagactttg atttgattca tttagattgt ccgcagcaac -continued

```
caaatggcta cgactgtgga atatatgttt gtatgaatac tctctatgga agtgcagatg cgccattgga ttttgattat aaagatgcga ttaggatgag aagatttatt gcccatttga ttttaaccga cgctttaaaa taagaattcg aagcttgatc cggctgctaa caaagcccga aaggaagctg agttggctgc tgccaccgct gagcaataac tagcataacc ccttggggcc tctaaacggg tcttgagggg ttttttgctg aaaggaggaa ctatatccgg atc
```

SEQ ID NO: 29 is vector AompT-cure:
```
ccgcgacagc gtctgccgca ttattcaaag cgatattcag cattactgga atctgcgaat gtcgccagt tcgctatgtt taagccccag cctgctcaaa aagaaattaa aaaacgaaaa taccagctat agccagattg tcacagagtg tcgtatgcgt tacgccgtac agatgttatt gatggataac aaaaatatca ctcaggtggc gcaattatgt ggctatagca gcacgtcgta ctttatctct gttttttaagg cgttttacgg cctgacaccg ttgaattatc tcgccaaaca gcgacaaaaa gtgatgtggt gaagggcaaa gcggaaacgg ataagacggg cataaatgag gaagaaatgg cgcgccctgc gaacgccaac taaaatttcc ccgaggtgaa aatcgccccg gggaataact agccatttca atgtaacaat taacccttaa aataaaccca gaaggttatt aactaaatca catagaaaac catcaattat agtatgtata aataggcga cagcaaccca attcaaatt aatggttcca gaatatcaca tcaaaaaaaa cgctgtataa tattataatt aacatgtaga caacttgtaa taaacattat cagtcaattg ttttgtttat tccatctgtg acgccgatta ttttctcaaa ataatgagat ggcgtgacac cataataatc tttaaatgca catatgaaat atgaagtact gttatagcc
```

SEQ ID NO: 30 is vector yibD-fadD-GentR
```
aactgaataa ttgcttgttt ttaaagaaaa agaaacagcg gctggtccgc tgtttctgca ttcttacggt aaagataaaa ataaatagtg acgcgcttcg cgaatccatg tgggagttta ttcttgacac agatatttat gatataataa ctgagtaagc ttaacataag gaggaaaaac atatgttacg cagcagcaac gatgttacgc agcagggcag tcgccctaaa acaaagttag gtggctcaag tatgggcatc attcgcacat gtaggctcgg ccctgaccaa gtcaaatcca tgcgggctgc tcttgatctt ttcggtcgtg agttcggaga cgtagccacc tactcccaac atcagccgga ctccgattac ctcgggaact tgctccgtag taagacattc atcgcgcttg ctgccttcga ccaagaagcg gttgttggcg ctctcgcggc ttacgttctg cccaagtttg agcagccgcg tagtgagatc tatatctatg atctcgcagt ctccggcgag caccggaggc agggcattgc caccgcgctc atcaatctcc tcaagcatga ggccaacgcg cttggtgctt atgtgatcta cgtgcaagca gattacggtg acgatcccgc agtggctctc tatacaaagt tgggcatacg ggaagaagtg atgcactttg atatcgaccc aagtaccgcc acctatgccc aggcatcaaa taaaacgaaa ggctcagtcg aaagactggg ccttcgttt tatctgttgt tgtcggtga acgctctcta ctagagtcac actggctcac cttcgggtgg gcctttctgc gtttatacac agctaacacc acgtcgtccc tatctgctgc cctaggtcta tgagtggttg ctggataacg tgcgtaattg tgctgatctc ttatatagct gctctcatta tctctctacc ctgaagtgac tctctcacct gtaaaaataa tatctcacag gcttaatagt ttccttaatac aaagcctgta aaacgtcagg ataacttcta tattcaggga gaccacaacg gtttccctct acaaataatt ttgtttaact ttcgtaaaga ggagaaatac tagttgaaga aggtttggct taaccgttat cccgcggacg ttccgacgga gatcaaccct gaccgttatc aatctctggt agatatgttt gagcagtcgg tcg
```

SEQ ID NO: 31 is vectoryibD-fadE::CC FatB1-ZeoR:
```
atgttttac atccactaca accatatcat cacaagtggt cagacctcct acaagtaagg ggcttttcgt tttactaaac tgaactttct gccggaatga cgctgatgcc acgaaagcta tcggtaagtt tcggacgcca ttcggtctta gcgcgcagca cttcgctacc tccttccagc tgcagcagat gttcgcaaac cagacctgct tcactgctac cgcccgatac cgtcgtcagg ctctgtaaca cactatccat ggtacattca cgacgatatt cgatggtaaa gctactgata tgatggcttt cgaagatgct atctggcacg gtttccagaa tccagtcaac gtatttgatg ttgttgacat gttggttgat gtccaaatca ttccagcgcg gggtaagtcc cccttggata taatcggcgg tgcctatcgtt caatttctgc ggttttttaa tttcctcatc tttcacggcc acgttgtcaa tgaaagccgg gccaatttca ccacgcactt cctccgggat tttagacaga cgacgggtac gagtgttcat cataacgctc aggctcgtgc agcgggtcag aatctcccc gttttgcaat cacgcactaa gaaatcgtga cgacgcccgt
```

-continued tattgccgga cgcccctacc caacactcca cttcaactgt gtcgcccat gccggatagc gctccacggc aacatgggta cgtttgacca cccaaataag atcacgctta gacatttcta acgtggtgcc aaaaccatct cccaggatac caacagattt ggcatggttg agtgccgcct cctgtaagtg gttcatgact gccacgatgc tagtactacg gtctgggccc acttcataag aacgatggc gaaggtgcgg cggaacacca gaccatgcgg accgaaatgg tcgtccagga gctgtggcgg atttggtttg ggtttccact ccagattcgt ccactgcttt tccgccgcac taaaaatggt agtgataacc gcgaataaca tgctccaatc cggcagtttt ttaagggatt cggtgtagct aaatttggta ccgttgatca ttttcaggct ggtctgtgca ttgccggcac gtaactgtaa gtcagagcta cgcggtttca tcccacgtcc atcgcgagcc agcataactg ctttcatcga acaaaaagcg ctcgccaggg atgtggttgc catctagtat ttctcctctt tacgaaagtt aaacaaaatt atttgtagag ggaaaccgtt gtggtctccc tgaatataga agttatcctg acgttttaca ggctttgtat taagaaacta ttaagcctgt gagatattat ttttacaggt gagagagtca cttcagggta gagagataat gagagcagct atataagaga tcagcacaat tacgcacgtt atccagcaac cactcataga cctagggcag cagatagggga cgacgtggtg ttagctgtgt tgacaattaa tcatcggcat agtatatcgg catagtataa tacgactcac tataggaggg ccatcatggc caagttgacc agtgccgttc cggtgctcac cgcgcgcgac gtcgccggag cggtcgagtt ctggaccgac cggctcgggt tctcccggga cttcgtggag gacgacttcg ccggtgtggt ccgggacgac gtgaccctgt tcatcagcgc ggtccaggac caggtggtgc cggacaacac cctggcctgg gtgtgggtgc gcggcctgga cgagctgtac gccgagtggt cggaggtcgt gtccacgaac ttccgggacg cctccgggcc ggccatgacc gagatcggcg agcagccgtg ggggcgggag ttcgccctgc gcgacccggc cggcaactgc gtgcactttg tggcagagga gcaggactga ggataagata acggagccga aaggctccgt ttctttatcc gctaattatt taaaattaaa gccatccgga tggttttc SEQ ID NO: 32:
gagaccacaa cggtttccct ctacaaataa ttttgtttaa ctttaaagag gagaaatact agatgcatca ccatcaccat cacatggcag atgaatcgga aaccgcggtt aaaccgccgg cgccgcccct tccgcagatg atggaaggta acggcaatgg gcatgagcat tgcagcgact gcgaaaacga ggaagataat tcgtataatc gtggtggact gtccccagcg aacgataccg gtgcaaaaaa aagaagaaa aagcagaaaa agaaaaaaga gaaaggcagc gaaaccgata gcgctcaaga tcagccagtg aaaatgaact cgttgcctgc tgagcgtatc caagaaattc agaaggcaat tgaactgttt agcgtgggtc aaggcccagc caaaacgatg gaggaagcga gcaaacgttc gtatcagttc tgggatacgc aaccggtgcc gaagctcggt gaagtggtga atacgcacgg gcctgttgag ccggataagg acaatattcg tcaggagcca tatacgctgc ctcagggttt cacttgggac gccctggacc tgggtgaccg tggtgtgctg aaagaactgt acaccctgct taatgagaat tatgtagaag atgacgacaa catgttccgt tttgactata gcccggaatt cctgttatgg gcactccgtc cgccgggttg gctgccgcag tggcattgcg gtgtccgcgt agtttcgagc cgtaaactcg taggtttcat cagtgcaatc ccggccaaca ttcatatcta tgacaccgag aaaaaaatgg tagaaattaa cttcctgtgt gttcataaga agttgcgtag caaacgcgta gcgcctgtcc tcattcgtga atcacgcgc cgcgtacatt tagaaggtat cttccaggca gtatatactg ctggcgtcgt gctcccaaaa ccggttggga cttgccgcta ttggcaccgc tctctgaatc cgcgtaagct gattgaagtt aaatttagcc atttgtcacg caacatgacc atgcagcgca ccatgaaact ttaccgtctg ccggaaaccc cgaaaactgc tggtttgcgc ccaatggaga cgaaagatat tcctgtcgtc catcagctgc tgacgcgtta tttaaaacag tttcacttaa ctcctgtcat gagccaggaa gaggttgaac attggtttta tccgcaagaa aacatcatcg acaccttcgt agtggagaat gcgaatggcg aagtcacgga ctttttatcc ttctatactt tgccgagcac catcatgaac catccgaccc ataaaagcct gaaggccgcg tactcatttt ataatgtcca cacgcagacc ccgttattgg atctgatgtc tgatgcgttg gtcctggcca aaatgaaagg tttcgacgtt tttaatgcgc tggacctgat ggagaacaaa acctttctgg aaaaattgaa attcggaatt ggcgatggta atctgcaata ctatctgtat aattggaaat gcccgtcgat gggtgcggaa aagttggtc tggtactgca gtagtaagac gaattctcta gatatcgc -continued SEQ ID NO: 33:
cagtccagtt acgctggagt ctgcccaggc atcaaataaa acgaaaggct cagtcgaaag actgggcctt tcgttttatc tgttgtttgt cggtgaacgc tctctactag agtcacactg gctcaccttc gggtgggcct ttctgcgttt atacacagct aacaccacgt cgtccctatc tgctgcccta ggtctatgag tggttgctgg ataacgtgcg taattgtgct gatctcttat atagctgctc tcattatctc tctaccctga agtgactctc tcacctgtaa aaataatatc tcacaggctt aatagtttct taatacaaag cctgtaaaac gtcaggataa cttctatatt cagggagacc acaacggttt ccctctacaa ataattttgt ttaactitta taaaatacta ttaaggagga tataatgtcg acagtgaag tcaaccagga agcgaaaccg gaagtgaaac cggaagtcaa acctgaaacg cacattaatc tgaaagtcag cgatggttcc agtgaaatct tcttcaaaat taaaaaaact acgccgttac gtcgtttgat ggaagcattt gcgaaacgcc agggcaagga aatggattcc ctccgcttct tatatgacgg gattcgtatc caagcagacc aaaccccgga ggacctggac atggaagaca acgatattat tgaagcacat cgcgaacaga ttggggcgg gaacgcagca gctgcgcgtc gccgtcgccg ctgcattacg ggggatgcac tggtcgcatt gcctgagggt gagagtgtgc gtattgcgga cattgtccct ggcgcgcgcc ccaactccga taacgcaatc gatctgaagg tcctggaccg ccacggcaat cccgtattag cagatcgttt attccattcg ggagaacatc cagtgtacac agtacgtact gtggaaggat tacgtgtcac cggaactgca aatcatccgc tgttgtgctt ggtagatgtt gcaggagtgc ctacactgtt gtggaaactg atcgacgaga tcaaaccagg cgattacgct gtaatccagc gtagtgcgtt ttcggtggac tgcgcgggtt ttgcgcgtgg caaacctgag ttcgccccta cgacttatac tgttggagtg cctggtctgg tccgtttttt agaagctcac catcgcgacc cagacgctca ggccatcgct gatgagttga cagacggtcg cttctattac gcaaaggtag cgagtgtaac agacgcaggg gtgcaacctg tctacagttt gcgtgttgac acagcggacc acgcatttat caccaatggc ttcgtctcgc atgcgacggg attgaccggg cttaactctg gattgactga aaatctctat tttcagggca tgtccccgat cctgggttac tggaaaatca aagggttagt gcagccaacc cgtctgttat agaatacct ggaggaaaaa tacgaggaac acctgtacga gcgcgatgaa ggcgataaat ggcgcaataa aaaattcgaa ctcgggctgg aattcccaaa cttaccctat tatattgatg gagatgttaa attgacccag tctatggcaa tcattcgcta tattgcagat aaacataaca tgttgggcgg ctgtcctaag gagcgcgcgg aaattagtat gctggaaggc gcggctgg atatccgcta tggtgttagc cgcattgcgt actcgaaaga ttttgagacg ctcaaagttg attttctgag taaactgcct gaaatgttaa agatgtttga agatcgcttg tgtcacaaaa cgtatttaaa tggtgatcat gtcacccatc cagactttat gctgtatgat gcgcttgatg tggttttgta catggatccg atgtgcctgg atgccttcc gaagctggtc tgtttcaaaa aacgcatcga ggctattccg caaatcgaca aatatctcaa atctagtaaa tacatcgcgt ggcctctgca gggctggcaa gcgacctttg gtggggcga tcatccgcca aaataatgaa ctgaccattt aaatcatacc tgacc SEQ ID NO: 34:
Xaa Xaa Xaa Xaa Xaa Xaa Xaa Xaa

SEQ ID NO: 35:
MSDSEVNQEAKPEVKPEVKPETHINLKVSDGSSEIFFKIKKTTPLRRLMEAF

AKRQGKEMDSLRFLYDGIRIQADQTPEDLDMEDNDIIEAHREQIGG

SEQ ID NO: 36
actgaccatt taaatcatac ctgacctcca tagcagaaag tcaaaagcct ccgaccggag gcttttgact tgatcggcac gtaagaggtt ccaactttca ccataatgaa ataagatcac taccgggcgt atttttgag ttatcgagat tttcaggagc taaggaagct aaaatgagcc atattcaacg ggaaacgtct tgctcgaggc cgcgattaaa ttccaacatg gatgctgatt tatatgggta taaatgggct cgcgataatg tcgggcaatc aggtgcgaca atctatcgat tgtatgggaa gcccgatgcg ccagagttgt ttctgaaaca tggcaaaggt agcgttgcca atgatgttac agatgagatg gtcaggctaa actggctgac ggaatttatg cctcttccga ccatcaagca ttttatccgt actcctgatg atgcatggtt actcaccact gcgatcccag ggaaaacagc attccaggta ttagaagaat atcctgattc aggtgaaaat attgttgatg cgctggcagt gttcctgcgc cggttgcatt cgattcctgt ttgtaattgt ccttttaacg gcgatcgcgt atttcgtctc -continued

```
gctcaggcgc aatcacgaat gaataacggt ttggttggtg cgagtgattt tgatgacgag cgtaatggct ggcctgttga acaagtctgg aaagaaatgc ataagctttt gccattctca ccggattcag tcgtcactca tggtgatttc tcacttgata accttatttt tgacgagggg aaattaatag gttgtattga tgttggacga gtcggaatcg cagaccgata ccaggatctt gccatcctat ggaactgcct cggtgagttt tctccttcat tacagaaacg cttttttcaa aaatatggta ttgataatcc tgatatgaat aaattgcagt ttcacttgat gctcgatgag ttttttctaat gagggcccaa atgtaatcac ctggctcacc ttcgggtggg cctttctgcg ttgctggcgt ttttccatag gctccgcccc cctgacgagc atcacaaaaa tcgatgctca agtcagaggt ggcgaaaccc gacaggacta taaagatacc aggcgtttcc ccctggaagc tccctcgtgc gctctcctgt tccgaccctg ccgcttaccg gatacctgtc cgcctttctc ccttcgggaa gcgtggcgct ttctcatagc tcacgctgta ggtatctcag ttcggtgtag tcgttcgct ccaagctggg ctgtgtgcac gaaccccccg ttcagcccga ccgctgcgcc ttatccggta actatcgtct tgagtccaac ccggtaagac acgacttatc gccactggca gcagccactg gtaacaggat tagcagagcg aggtatgtag gcggtgctac agagttcttg aagtggtggc ctaactacgg ctacactaga agaacagtat ttggtatctg cgctctgctg aagccagtta cctcggaaaa agagttggta gctcttgatc cggcaaacaa accaccgctg gtagcggtgg ttttttttgt tgcaagcagc agattacgcg cagaaaaaaa ggatctcaag aagatccttt gattttctac cgaagaaagg cccacccgtg aaggtgagcc agtgagttga ttgcagtcca gttacgctgg agtctgccca ggcatcaaat aaaacgaaag gctcagtcga aagactgggc ctttcgtttt atctgttgtt tgtcggtgaa cgctctctac tagagtcaca ctggctcacc ttcgggtggg cctttctgcg tttatacaca gctaacacca cgtcgtccct atctgctgcc ctaggtctat gagtggttgc tggataacgt gcgtaattgt gctgatctct tatatagctg ctctcattat tctctaccc tgaagtgact ctctcacctg taaaaataat atctcacagg cttaatagtt tcttaataca aagcctgtaa aacgtcagga taacttctat attcaggag accacaacgg tttccctcta caaataattt tgtttaactt taaagaggag aaatactaga tgtcggacag tgaagtcaac caggaagcga accggaagt gaaaccggaa gtcaaacctg aaacgcacat taatctgaaa gtcagcgatg gttccagtga atcttcttc aaaattaaaa aaactacgcc gttacgtcgt ttgatgaag catttgcgaa acgccagggc aaggaaatgg attccctccg cttcttatat gacgggattc gtatccaagc agaccaaacc ccggaagatc tggacatgga agacaacgat attattgaag cacatcgcga acagattggg ggcgggaacg cagcatctgc gcgccgcgaa aatctctatt ttcagggcat gtccccgatc ctgggttact ggaaaatcaa agggttagtg cagccaaccc gtctgttatt agaatacctg gaggaaaaat acgaggaaca cctgtacgag cgcgatgaag gcgataaatg gcgcaataaa aaattcgaac tcgggctgga attcccaaac ttaccctatt atattgatgg agatgttaaa ttgacccagt ctatggcaat cattcgctat attgcagata acataacat gttgggcggc tgtcctaagg agcgcgcgga aattagtatg ctggaaggcg cggtgctgga tatccgctat ggtgttagcc gcattgcgta ctcgaaagat tttgagacgc tcaaagttga ttttctgagt aaactgcctg aaatgttaaa gatgtttgaa gatcgcttgt gtcacaaaac gtatttaaat ggtgatcatg tcacccatcc agactttatg ctgtatgatg cgcttgatgt ggttttgtac atggatccga tgtgcctgga tgccttttccg aagctggtct gtttcaaaaa acgcatcgag gctattccgc aaatcgacaa atatctcaaa tctagtaaat acatcgcgtg gcctctgcag ggctggcaag cgacctttgg tggggcgat catccgccaa aatgataatc gcgcaaaaaa ccccgcttcg gcggggtttt ttcgcacgtc tccatcgctt gccaagttg tgaagcacag ctaacaccac gtcgtcccta tctgctgccc taggtctatg agtggttgct ggataacgcc acggaaatca ataacctgaa gatatgtgcg acgagctttt cataaatctg tcataaatct gacgcataat gacgtcgcat taatgatcgc aacctattta ttatattcag ggagaccaca acggtttccc tctacaaata attttgttta actttgcttc aatctaaatt agtaaggagg tagtcaatga caaatcctgg tgtaagtgcc tggcaagtta ataccgcata taccgctggg cagttagtca cttataacgg caagacctac aagtgcttgc agcctcacac atccttggca ggttgggaac cgtccaatgt acccgccctt tggcaacttc agggctctgc cggtagtgcg gcgggttccg gtgaatttaa ctcgttgcct gctgagcgta tccaagaaat tcagaaggca attgaactgt ttagcgtggg tcaaggccca gccaaaacga tggaggaagc gagcaaacgt tcgtatcagt tctgggatac gcaaccggtg ccgaagctcg gtgaagtggt gaatacgcac gggcctgttg agccggataa ggacaatatt cgtcaggagc catatacgct gcctcagggt ttcacttggg
```

```
acgccctgga cctgggtgac cgtggtgtgc tgaaagaact gtacaccctg cttaatgaga attatgtaga agatgacgac aacatgttcc gttttgacta tagcccggaa ttcctgttat gggcactccg tccgccgggt tggctgccgc agtggcattg cggtgtccgc gtagtttcga gccgtaaact cgtaggtttc atcagtgcaa tcccggccaa cattcatatc tatgacaccg agaaaaaaat ggtagaaatt aacttcctgt gtgttcataa gaagttgcgt agcaaacgcg tagcgcctgt cctcattcgt gaaatcacgc gccgcgtaca tttagaaggt atcttccagg cagtatatac tgctggcgtc gtgctcccaa aaccggttgg gacttgccgc tattggcacc gctctctgaa tccgcgtaag ctgattgaag ttaaatttag ccatttgtca cgcaacatga ccatgcagcg caccatgaaa ctttaccgtc tgccggaaac cccgaaaact gctggtttgc gcccaatgga gacgaaagat attcctgtcg tccatcagct gctgacgcgt tatttaaaac agtttcactt aactcctgtc atgagccagg aagaggttga acattggttt tatccgcaag aaaacatcat cgacaccttc gtagtggaga atgcgaatgg cgaagtcacg gactttttat ccttctatac tttgccgagc accatcatga accatccgac ccataaaagc ctgaaggccg cgtactcatt ttataatgtc cacacgcaga ccccgttatt ggatctgatg tctgatgcgt tggtcctggc caaaatgaaa ggtttcgacg tttttaatgc gctggacctg atggagaaca aaacctttct ggaaaaattg aaattcggaa ttggcgatgg taatctgcaa tactatctgt ataattggaa atgccgtcg atgggtgcgg aaaaagttgg tctggtactg cagtagtaa
```

SEQ ID NO: 37:
GNAAAARR

DETAILED DESCRIPTION

The present application is directed to a genetically modified organism, e.g., modified E. coli, and a corresponding fermentation process that may provide, for example, single pot, facile, commercially relevant production of N-terminally fatty acylated proteins and peptides, based on in vivo N-terminal acylation. A combination of expression vectors and metabolic engineering approaches may provide the production and activation of substrates for protein acylation or lipidation. This may include, for example, one or more of: (1) the expression of a target protein to be acylated and subsequent modification to expose a fatty acylation substrate, (2) in vivo generation of fatty acids and activation into corresponding fatty acyl-CoAs and (3) expression of an acyl transferase that may catalyze the acylation reaction.

A genetically modified microorganism may include a first gene encoding an acyl transferase, a second gene encoding a peptide or protein to by acylated, a third gene encoding a enzyme to remove a N-terminal tag from the second gene, a gene encoding a homologous acyl-CoA synthase, a gene encoding a heterologous acyl-CoA thioesterase, and deletion of a gene that mitigates degradation of acyl-CoA.

Figure 1:
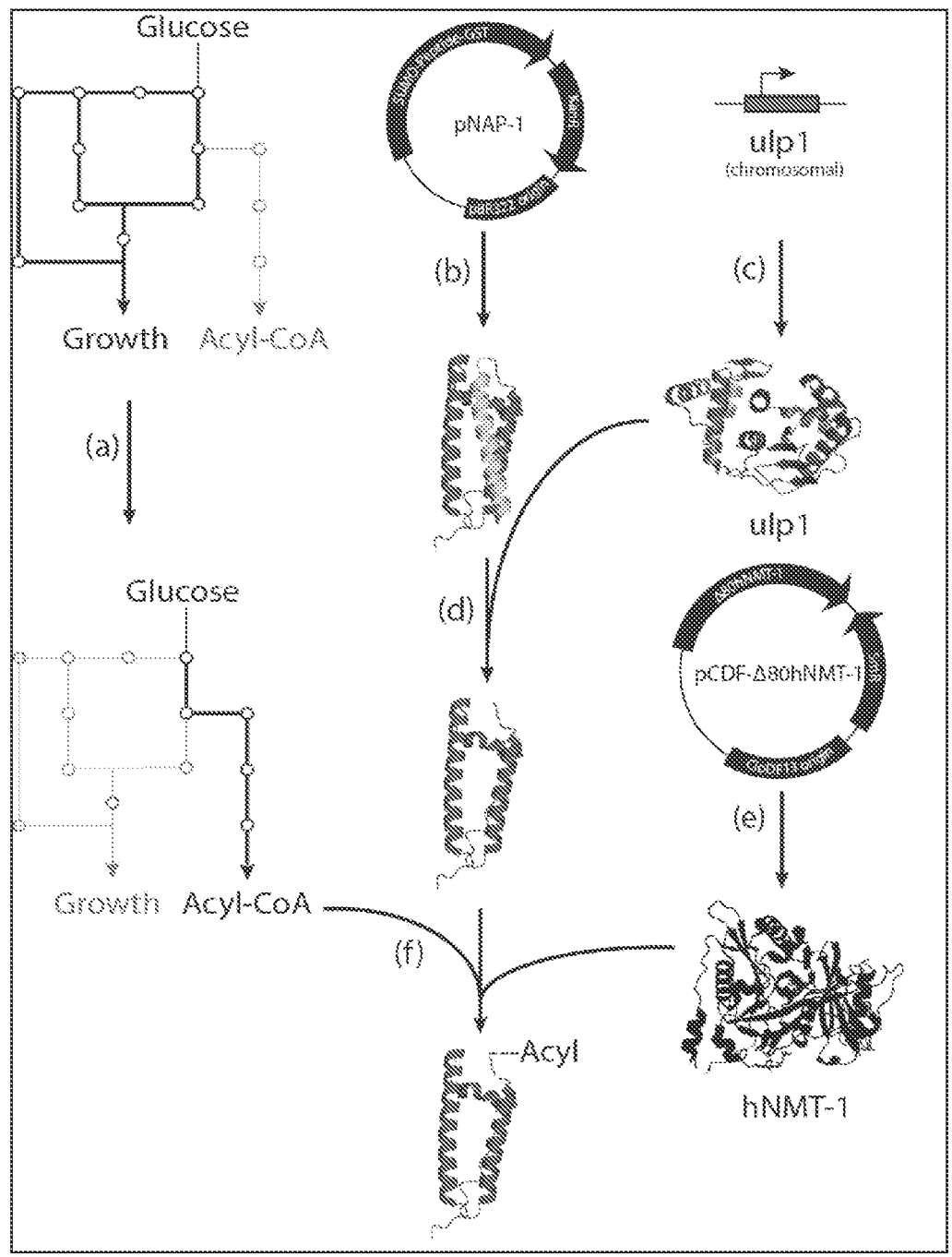
FIG. 1 is a schematic depicting some of the embodiments of the in vivo protein N-acylation through dynamic metabolic control of acyl-CoA biosynthesis.

An exemplary embodiment is shown in FIG. 1, where (1) a target peptide for acylation may be encoded by a gene that may also encode a N-terminal tag and substrate and a C-terminal tag. The encoded gene may be represented as, for example SUMO-peptide-Glutathione S-transferase (GST). The protein target may be encoded by a gene that may be heterologously expressed in the genetically modified microorganism. For example, the target protein may be cloned into vector pNAP-1(N-terminal acylation of proteins) bearing a high copy ColE1 origin of replication and a kanamycin resistance marker. Such a vector may include, e.g., the low phosphate inducible E. coli yibD gene promoter operatively linked to the gene encoding SUMO-peptide-GST. The vector may also include a ribosomal binding site, e.g., to drive target protein expression. The ribosomal binding site may be optimized to drive target protein expression. A N-terminal SUMO tag, cleavable with ulp1 hydrolase from Saccharomyces cerevisiae, may also be included to enhance expression. In addition to increasing expression, the SUMO tag may function as a cleavage moiety to reveal a N-terminal recognition sequence, e.g., GNAAAARR (SEQ ID NO: 36). Such a sequence may be a substrate for an acyl transferase such as human N-myristol transferase-1 (hNMT-1) to provide N-acylation of the protein. For example, the target peptide may be operatively linked to a C-terminal tag such as GST to provide, for example, protein purification and quantification. Any peptide or protein may be the N-acylation target of interest and may be cloned into the SUMO-peptide-GST gene. Other suitable recognition sequences may be used.

As shown in FIG. 1, (3) a fatty acyl transferase may also be heterologously expressed in the genetically modified microorganism. For example, plasmid pCDF-hNMT-1, derived from pCDF-1b, contains the gene for human N-myristoyl transferase 1 (hNMT-1), with an 80 amino acid deletion to improve myristoylation. The vector plasmid may also bear, for example, the high copy CloDF13 origin and a spectinomycin resistance cassette. The vector plasmid may be constructed with the yibD gene promoter operatively linked to the acyl transferase gene to drive hNMT-1 expression upon phosphate depletion.

Also shown in FIG. 1 is (2) the generation of fatty acids and corresponding activation into fatty acyl-CoAs. Such fatty acyl-CoAs may be metabolically engineered for increased and/or inducible production and accumulation of the fatty acyl-CoAs. A system such as that described in FIG. 1 shows a genetically modified microorganism that may provide one or more of: a target protein or peptide to be N-acylated; an enzyme to acylate the target peptide or protein; and a fatty acyl CoA source for use by the acylating enzyme in vivo, e.g., without the need for exogenously added fatty acids.

Figure 3:
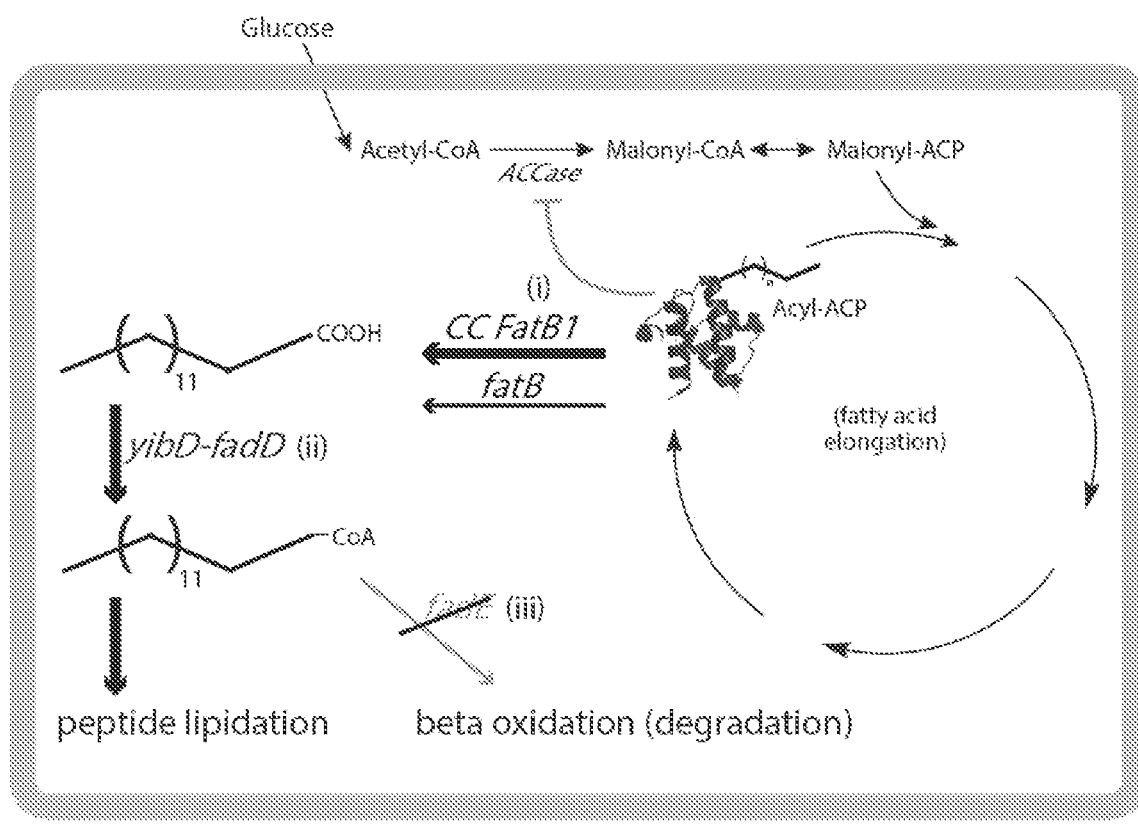
FIG. 3 is a schematic depicting an embodiment of the in vivo protein N-acylation through dynamic acyl-CoA production in a myristoyl-CoA producing strain.

FIG. 3 shows an exemplary embodiment of the genetically modified microorganism to provide inducible accumulation production of fatty acyl CoA. Inducible fatty acyl-CoA production may be accomplished, e.g., by (iii) deleting a native fadE gene from the E. coli chromosome, and (i) replacing the deleted native gene with, e.g., an inducible acyl-ACP thioesterase from Cinnamomum camphorum with a preference for myristoyl (C14 acyl) substrates. Together these modifications mitigate fatty acyl-CoA beta oxidation and provide the conversion of biosynthetic fatty acyl-ACPs into intracellular free fatty acids. Additionally or alternatively, (ii) the native E. coli fadD gene encoding a fatty acyl-CoA synthetase is induced by replacement of the native promoter with the low phosphate inducible yibD gene promoter.

Acyl Transferase

The genetically modified microorganisms described herein may include a first gene that encodes an acyl transferase. This acyl transferase may catalyze the N-acylation of a target protein or peptide (3). The first gene may encode a $C_8$-$C_{18}$ acyl transferase.

As exemplified in FIG. 1, the acyl transferase may be, e.g., human N-myristoyl transferase. In various embodiments, any acyl transferase that may recognize a target to be acylated and an acyl-CoA may be suitable. For example, acyl transferases that recognize a N-terminal tag or substrate may be used in some embodiments. Acyl transferases may be target protein sequence or acyl-CoA specific. N-Myristoyl transferase, a palmitoyl transferase, any $C_8$-$C_{18}$ transferase, and N-myristoyl transferases may be encompassed as embodiments of the acyl transferase of the invention.

The following Examples of suitable glycylpeptide N-tetradecanoyltransferase proteins may be used as the acyl transferase in an embodiment of the genetically modified microorganism may include one or more of (by Uniprot number): P30419, P14743, Q9LTR9, P30418, 070310, P31717, Q8TFN1, 061613, 043010, Q8K1Q0, 074234, Q9UVX3, Q75EK2, A7YT82, Q5RAF3, Q4I061, Q6CMK4, Q7S3C8, Q6C7G2, Q6BJF4, Q4PB56, Q553B6, P34809, P34763, P0CP20, and Q81LW6.

Modification of Acyl-CoA Substrate Specificity for Acyl Transfer Reaction

Any Ce-Cis acyl-CoAs may be recognized by a N-acyl transferase with modified substrate specificity. For example, mutating acyl-CoA binding site (amino acids 30-50, 100-110, 160-210, or 420-430) of yeast N-myristoyltransferase may be used to alter substrate specificity. Likewise, mutating the residues of the acyl-CoA binding site (amino acids 240-290) of human N-myristoyltransferase 1 may alter substrate specificity. Suitable wild-type enzymes exist that are known to react with acyl-CoAs other than myristoyl-CoA.

N-Terminal Acylation of Peptides or Proteins

The genetically modified microorganisms described herein may include a second gene that encodes a peptide or protein. This peptide or protein may be (i) the target protein to be N-acylated. In some embodiments, prior to acylation, the peptide or protein may be subject to a modification of the peptide or protein to expose a fatty acylation substrate. Any heterologous gene encoding a peptide of protein of interest may be used with the present invention. Similarly, any homologous gene, for example, those modified to be operatively connected to an inducible promoter may also be suitable acylation peptide or protein targets.

Suitable peptide and protein substrates for acylation, such as existing therapeutic peptides or proteins or peptides or proteins of potential therapeutic value may include, e.g., one or more of: somatotropin (Uniprot #P01241), glucagon (Uniprot #P01275), insulin (Uniprot #P01308), fibroblast growth factor 21 (Uniprot #Q9NSA1), fibroblast growth factor 1 ((Uniprot #P05230), fibroblast growth factor 2 (Uniprot #P09038), fibroblast growth factor 7 (Uniprot #P21781), fibroblast growth factor 18 (Uniprot #O76093), fibroblast growth factor 19 (Uniprot #O95750), enkephalin (Uniprot #P01210), galanin (Uniprot #P22466), gastric inhibitory peptide (Uniprot #P09681), pancreatic prohormone (Uniprot #P01298), calcitonin (Uniprot #P01258), neuropeptide W (Uniprot #Q8N729), neuropeptide Y (Uniprot #P01303), hirudin (Uniprot #P01050), coagulation factor VIII (Uniprot #P00451), coagulation factor IX (Uniprot #P00740), tissue plasminogen activator (Uniprot #P00750), follicle-stimulating hormone (Uniprot #P01215), erythropoietin (Uniprot #P01588), granulocyte colony-stimulating factor (Uniprot #P09919), interferon (Uniprot #P01563), and asparaginase (Uniprot #P06608).

Modification of Peptide Substrate Specificity for Acyl Transfer Reaction

In some embodiments, a tag and/or a substrate may be added to the N-terminus of the target peptide or protein. For example, the vector pNAP-1(N-terminal acylation of proteins), or an equivalent vector, may include a gene encoding at least one tag-substrate-peptide.

The Acyltransferase Substrate

The peptide substrate for the acyl N-terminal transfer reaction may include peptides with the sequence X1X2X3X4X5X6X7X8 (SEQ ID NO: 34) where X1 may be glycine, X2 and X5 may be small uncharged residues, e.g., other than proline; X6 may be any residue, e.g., other than proline and X3, X4, X7 and X8 may be any residues. Specificity may be broadened using N-acyl transferases corresponding mutations as described above for acyl substrate specificity modification. The substrate for fatty acylation may be, for example, a naturally occurring sequence found inherently in the peptide of protein encoded by the second gene. The substrate may be a naturally occurring sequence represented by an oligonucleotide operatively linked to the second gene encoding a peptide or protein to be acylated. When cloned in this manner, the resultant expression product is a peptide or protein with an acylation substrate at the N-terminus. The substrate may also encode a heterologous substrate.

Using a Protease to Expose a N-Terminal Peptide Substrate for the Acyl Transfer Reaction In another embodiment, a protease, e.g., a protein naturally occurring in the microorganism, or an expressed heterologous protease may be used to prepare the N-terminus of the target protein or peptide for the N-terminal acylation reaction.

For example, a microorganism may be used that encodes a native or heterologous methionine aminopeptidase, for example E coli methionine aminopeptidase or human methionine aminopeptidase (Uniprot #P0AE18 and P50579, respectively) to remove a methionine when the following amino acid may be, for example, alanine, glycine, senne, threonine, asparagine, aspartate, isoleucine, proline, valine or leucine.

N-Terminal Tag

In an exemplary embodiment, the genetically modified microorganism may encode a ubiquitin-like-specific protease such as ubiquitin-like-protease 1 (Uniprot #Q02724). Ubiquitin-like protease 1 is able to remove a N-terminal peptide sequence such as a SUMO tag with sequence:

(SEQ ID NO: 35)
MSDSEVNQEAKPEVKPEVKPETHINLKVSDGSSEIFFKIKKTTPLRRLME

AFAKRQGKEMDSLRFLYDGIRIQADQTPEDLDMEDNDIIEAHREQIGG.

In yet other exemplary embodiments, the starting amino acid on the peptide or protein substrate may exclude proline.

In some embodiments, a first oligonucleotide encoding a N-terminal protein tag may be operatively linked to the second gene so that upon expression of the second gene, a N-terminal protein tag may be linked to a peptide or protein encoded by the second gene. For example, the N-terminal tag may be a SUMO tag, a FLAG (octapeptide), a TRx (thioredoxin), a TAP (tandem affinity purification tag), a Lucy tag (fluorescent protein), and the like. Any appropriate cleavable N-terminal tag may be operatively linked to the N-acylation target peptide or protein. Further, the genetically modified microorganism may naturally endode a protease for removal of the N-terminal tag. Additionally or alternatively, a heterologously expressed protease may be expressed by a genetically modified microorganism. The protease may be, for example, an enterokinase, a TEV (tobacco etch virus), a thrombin, a GST-protease fusion protein, another substrate specific protease, and the like.

C-Terminal Protein Tags

A suitable, cleavable C-terminal protein tag may aid in the purification or expression of the acylation target peptide or protein. For example, glutathione S-transferase may be found in the gene for expression of the acylation target protein or peptide as shown in FIG. 1. Suitable C-tags may be substituted for GST including, for example, a maltose binding protein, calmodulin binding peptide, his-patch thio-fusion, tap affinity purification, epitope tags, reporter tags such as alkaline phosphatase, modified haloalkane dehalogenase, SUMO, serine proteinase such as subtilisin, postsynaptic density protein, streptavidin/biotin-based tags, chitin binding domain tag, and polyhistidine.

Inducible Production and Accumulation of Acyl-CoA

The production and accumulation of at least one acyl-CoA compared to the corresponding native microorganism may be brought about, e.g., by one or more of: inducing expression of a homologous acyl-CoA synthase; expressing a heterologous acyl-CoA thioesterase; and mitigating degradation of the acyl-CoA.

Acyl-CoA Thioesterase Expression

Acyl-CoAs of different lengths, e.g., $C_8$-$C_{18}$ acyl groups such as C8, C10, C12, C14, C16, and C18 may be biosynthesized by varying the gene encoding the acyl-acp thioesterase. Table 1 summarizes examples of different acyl-acp thioesterases.

TABLE 1

| Gene ACC NO./ Uniprot NO. | Preferred acyl chain length |
|---|---|
| AAC49179 | C8 |
| AAB71731 | C8 |
| AAG43857 | C16 |
| AAG43858 | C14/C16 |
| EER87824 | C14 |
| EER88593 | C14 |
| GE3ESU6 | C14 |
| GE3ESU8 | C16 |
| GE3ESU7 | C14 |
| CAH09236 | C12/C14 |
| ABR43a01 | C14 |
| AAO77182 | C14 |
| ABG82470 | C8 |
| EEG55387 | C14 |
| EET61113 | C8 |
| Cuphea leptopoda Fatb2 | C10 |
| EH147208.1 | C18 |
| Q39513 | C16 |
| G3ESU9 | C8 |
| G3ESV0 | C14 |
| G3ESV1 | C14 |
| AAD42220 | C14 |
| EDQ65090 | C14 |
| EER96252 | C16 |
| EES11622 | C14 |
| EEH52851 | C14 |
| ACL08376 | CB |
| EDV7752a | C12 |
| BAH81730 | C14 |
| ABJ63754 | C8 |
| CAD663310 | C8 |
| EE182564 | C8 |
| CAE80300 | C8 |
| ABN5426a | C14 |
| Q39554 | C14 |
| Q9SQ13 | C16 |

In some embodiments, a heterologous thioesterase may lead to increased fatty acid production. For example, a genetically modified microorganism with a heterologous thioesterase such as C. camphora acyl-ACP thioesterase may increase myristic acid production via cleavage of myristate from myristoty 1-ACP. Further, for example, the level of myristic acid produced may be increased by alleviating the inhibition of ACCase by acyl-ACPs (FIG. 3). A thioester of any substrate specificity may be used. Further, the substrate specificity of a known thioester may be modified. Any thioesters that would generally lead to the overproduction of a fatty acyl chain that is 8 to 18 carbons in length, e.g., Ce-Cis acyl groups such as C8, C10, C12, C14, C16, and C18, may be used in the genetically modified organism as part of the modified acyl-CoA biosynthetic pathway. Acyl-CoA synthase Fatty acids overproduced by the action of the thioesterasemay be activated by native or heterologous acyl-CoA synthase such as E. coli acyl-CoA synthase (encoded by fadD) with native or modified substrate specificity. For example, mutations on amino acid residues (4, 5, 9, 338, 372, 376, 447, 451) of fadD have been described as resulting in modified substrate specificity.

The acyl-CoA synthase may be encoded by a heterologous gene or by overexpression of the fadD (acyl-CoA synthetase) may occur by replacing the native promoter for the low phosphate inducible yibD gene promoter that results in accumulation of myristoyl-CoA. Accordingly, expression of the enzyme may occur under the fermentation conditions of low phosphate.

The thioesterase and acyl-Co synthase genes may be expressed on exogenous DNA or chromosomally.

Mitigation of Acyl-CoA Degradation

A third component of the modified acyl-CoA biosynthetic pathway of a genetically modified organism may include deletion the fadE gene. Deletion may mitigate or eliminate the beta oxidative pathway of acyl-CoAs, making the acyl-CoAs available for peptide acylation.

In various embodiments, a genetically modified microorganism is provided. The genetically modified microorganism may include a first gene that encodes an acyl transferase. The genetically modified microorganism may include a second gene that encodes a peptide or protein. One or both of the first and second gene may be heterologous with respect to a corresponding native microorganism. The genetically modified microorganism may include a modified acyl-CoA biosynthetic pathway. Compared to a native acyl-CoA biosynthetic pathway in the native microorganism, the modified acyl-CoA biosynthetic pathway may be configured for one or more of: inducible biosynthesis of an acyl-CoA and over-accumulation of the acyl-CoA. The genetically modified microorganism may be effective upon fermentation to cause acylation of the peptide or protein by the acyl transferase using the acyl-CoA to provide a N-acylated peptide or protein product. The genetically modified organism may be employed in any method described herein. The genetically modified organism may be employed to produce any N-acylated peptide or protein described herein.

In some embodiments, the genetically modified microorganism may be characterized by inducible production of one or more of: the acyl transferase encoded by the first gene, the peptide or protein encoded by the second gene, and the acyl-CoA. For example, the genetically modified microorganism may include a yibD or ugpB gene promoter. The yibD gene promoter may be operatively linked to one or more of, e.g.: the first gene; the second gene; and at least one modified acyl-CoA biosynthetic pathway gene corresponding to the modified acyl-CoA biosynthetic pathway. One or more of the first, second, and the at least one modified acyl-CoA biosynthetic pathway gene gene may be inducible by phosphate depletion of the fermentation medium In several embodiments, the first gene may encode a $C_8$-$C_{18}$ acyl transferase, e.g., one of C8, C10, C12, C14, C16, and C18. The first gene may encode a human acyl transferase. The first gene may encode, e.g., human N-myristoyl transferase 1. The first gene may encode one of a myristoyl transferase, a palmitoyl transferase, a N-myristoyl tranferase, and a glycylpeptide N-tetradecanoyl transferase. The first gene may encode a glycylpeptide N-tetradecanoyl transferase. The transferase, e.g., the glycylpeptide N-tetradecanoyl transferase, may include a mutation in an acyl-CoA binding site. The transferase, e.g., the glycylpeptide N-tetradecanoyl transferase, glycylpeptide N-tetradecanoyl transferase, may be characterized by a modified acyl-CoA substrate specificity corresponding to the mutation. An example of the first gene may include SEQ. ID NO. 32.

In various embodiments, the second gene may encode, e.g., one of: somatotropin, glucagon, insulin, fibroblast growth factor 21, fibroblast growth factor 1, fibroblast growth factor 2, fibroblast growth factor 7, fibroblast growth factor 18, fibroblast growth factor 19, enkephalin, galanin, gastric inhibitory peptide, pancreatic prohormone, calcitonin, neuropeptide W, neuropeptide Y, hirudin, coagulation factor VIII, coagulation factor IX, tissue plasminogen activator, follicle-stimulating hormone, erythropoietin, granulocyte colony-stimulating factor, interferon, and asparaginase. The second gene may encode a human peptide or protein. An example of the second gene may include SEQ. ID NO. 33.

In some embodiments, the genetically modified microorganism may include a first oligonucleotide that encodes a protein tag. The protein tag may be one or more of: a SUMO tag, a FLAG (octapeptide), a TRx (thioredoxin), a TAP (tandem affinity purification tag), a fluorescent protein. The first oligonucleotide may be operatively linked to the second gene so that expression using the first oligonucleotide and the second gene may result in a product that may include the protein tag operatively linked to the N-terminus of the peptide or protein. The genetically modified microorganism may include a third gene. The third gene may encode a cleaving enzyme configured to cleave the protein tag from the peptide or protein. The third gene may be one or more of heterologous with respect to the native microorganism and inducible. The third gene may encode the cleaving enzyme including one of: ulp1, enterokinase, a TEV (tobacco etch virus), a thrombin, GST-protease fusion protein, another substrate specific protease, and the like. An example of the third gene may include SEQ. ID NO. 28.

In several embodiments, the genetically modified microorganism may include a second oligonucleotide that may encodes a C-terminal tag. The second oligonucleotide may be operatively linked to the second gene so that expression using the second oligonucleotide and the second gene may result in a product that may include the C-terminal tag and the peptide or protein. The C-terminal tag may be, for example, one of: a glutathione S-transferase, a maltose binding protein, a calmodulin binding peptide, a his-patch thiofusion, a tap affinity purification tag, an epitope tag, a reporter tag such as alkaline phosphatase, a modified haloalkane dehalogenase, SUMO, a serine proteinase such as subtilisin, a post-synaptic density protein, a streptavidin/biotin-based tag, a chitin binding domain tag, and a polyhistidine.

In various embodiments, the genetically modified microorganism may include a third oligonucleotide that encodes a substrate. The third oligonucleotide may be operatively linked to the first oligonucleotide and the second gene so that expression using the first oligonucleotide, the third oligonucleotide, and the second gene produces a product that may include the protein tag, the substrate, and the peptide or protein. The substrate may be, for example, a substrate for a glycylpeptide N-tetradecanoyltransferase. An example of the substrate encoded by the third oligonucleotide may include SEQ. ID NOS. 36.

In some embodiments, the genetically modified microorganism may include a fourth oligonucleotide that may encode, e.g., a methionine aminopeptidase sensitive protease tag. The fourth oligonucleotide may be operatively linked to the second gene so that expression using the fourth oligonucleotide and the second gene may produce a product that may include the methionine aminopeptidase sensitive protease tag operatively linked to the N-terminus of the peptide or protein. The genetically modified microorganism may include a third gene that encodes, e.g., a cleaving enzyme. The cleaving enzyme may be configured to cleave the methionine aminopeptidase sensitive protease tag from the peptide or protein. The third gene may be homologous or heterologous. The third gene may be inducible.

In several embodiments, the modified acyl-CoA biosynthetic pathway may be configured to induce expression of a homologous acyl-CoA synthase. The modified acyl-CoA biosynthetic pathway may be configured to express a heterologous acyl-CoA thioesterase. The modified acyl-CoA biosynthetic pathway may be configured to mitigate degradation of the acyl-CoA. The genetically modified microorganism may include, for example, deletion of a gene corresponding to an acyl-CoA degradation pathway of the corresponding native microorganism. Deletion of the gene may be effective to mitigate degradation of the acyl-CoA. The gene may encode, for example, fadE.

In various embodiments, the genetically modified microorganism may include an inducible promoter. The inducible promoter may be effective to induce expression of the homologous acyl-CoA synthase. The inducible promoter may be, for example, a yibD gene promoter configured to induce expression of the homologous acyl-CoA synthase in the presence of phosphate depletion of a fermentation medium For example, the expression of the heterologous acyl-CoA thioesterase may be inducible. The genetically modified microorganism may include a ayibD gene promoter operatively linked to a gene for the heterologous acyl-CoA thioesterase effective to induce expression of the heterologous acyl-CoA thioesterase, e.g., in the presence of phosphate depletion of a fermentation medium The heterologous acyl-CoA thioesterase may be selected for a preference for myristoyl substrates. The heterologous acyl-CoA thioesterase may be, for example, derived from *Cinnamomum camphorum*. In some embodiments, the microorganism may be configured to induce expression of the homologous acyl-CoA synthase, to express the heterologous acyl-CoA thioesterase, and to mitigate degradation of the acyl-CoA.

In various embodiments, a method of in vivo acylation of a target peptide or protein in a genetically modified microorganism is provided. The method may include expressing an acyl transferase encoded by a first gene. The method may include expressing a peptide or protein encoded by a second gene. One or both of the first and second gene may be heterologous compared to a corresponding native microorganism. The method may include producing an acyl-CoA using a modified acyl-CoA biosynthetic pathway. The method may include fermenting the microorganism under conditions effective to cause acylation of the peptide or protein by the acyl transferase using the acyl-CoA to provide a N-acylated peptide or protein product.

In some embodiments, the method may include inducing one or more of: the expression of the acyl transferase; the expression of the peptide or protein, and the synthesis of the acyl-CoA. The inducing may include auto-inducing by phosphate depletion of the microorganism medium. The method may include causing acylation of the peptide or protein using a $C_8$-$C_{18}$ acyl transferase, e.g., one of C8, C10, C12, C14, C16, and C18. The method may include causing acylation of the peptide or protein using a human acyl transferase. The method may include causing acylation of the peptide or protein using human N-myristoyl transferase 1. The method may include causing acylation of the peptide or protein using one of a myristoyl transferase, a palmitoyl transferase, a N-myristoyl transferase, a glycylpeptide N-tetradecanoyl transferase, and a glycylpeptide N-tetradecanoyl transferase. The transferase, e.g. the glycylpeptide N-tetradecanoyl transferase, may include a mutation in an acyl-CoA binding site.

In several embodiments, the method may include expressing the second gene encoding a human peptide or protein. The second gene may, for example, encode one of: somatotropin, glucagon, insulin, fibroblast growth factor 21, fibroblast growth factor 1, fibroblast growth factor 2, fibroblast growth factor 7, fibroblast growth factor 18, fibroblast growth factor 19, enkephalin, galanin, gastric inhibitory peptide, pancreatic prohormone, calcitonin, neuropeptide W, neuropeptide Y, hirudin, coagulation factor VIII, coagulation factor IX, tissue plasminogen activator, follicle-stimulating hormone, erythropoietin, granulocyte colony-stimulating factor, interferon, and asparaginase.

In various embodiments, the method may include expressing a protein tag operatively linked to the N-terminus of the peptide or protein. The method may include expressing a cleaving enzyme under conditions effective to cleave the protein tag from the peptide or protein. The method may include expressing the protein tag as one of: a SUMO tag, a FLAG (octapeptide), a TRx (thioredoxin), a TAP (tandem affinity purification tag), and a fluorescent protein. The method may include expressing the cleaving enzyme as one of: ulp1, enterokinase, a TEV (tobacco etch virus), a thrombin, a GST-protease fusion protein (e.g., a fusion protein of glutathione S-transferase and recombinant human rhinovirus (HRV 3C) protease, such as PRESCISSION™, GE Healthcare Bio-Sciences AB, Uppsala, Sweden), another substrate specific protease, and the like. The method may include expressing a C-terminal tag operatively linked to the peptide or protein such that fermenting the microorganism under conditions may be effective to cause acylation to provide the N-acylated peptide or protein product including the C-terminal tag. The method may include purifying the N-acylated peptide or protein product using the C-terminal tag. The C-terminal tag may be, for example, one of: a glutathione S-transferase, a maltose binding protein, a calmodulin binding peptide, an his-patch thiofusion, a tap affinity purification tag, an epitope tag, a reporter tag such as alkaline phosphatase, a modified haloalkane dehalogenase, SUMO, a serine proteinase such as subtilisin, a post-synaptic density protein, a streptavidin/biotin-based tag, a chitin binding domain tag, and a polyhistidine.

In some embodiments, the method may include expressing a methionine aminopeptidase sensitive protease tag operatively linked to the N-terminus of the peptide or protein. The method may include expressing a cleaving enzyme. The method may include cleaving the methionine aminopeptidase sensitive protease tag from the N-terminus of the peptide or protein. The method may include expressing a substrate operatively linked between the protein tag and the peptide or protein to produce a product including the protein tag, the substrate, and the peptide or protein. The substrate may be a substrate for a transferase, e.g., a glycylpeptide N-tetradecanoyltransferase.

In several embodiments, the modified acyl-CoA biosynthetic pathway may include deletion of a gene that encodes fadE. The method may include synthesizing the acyl-CoA using the modified acyl-CoA biosynthetic pathway. The modified acyl-CoA biosynthetic pathway may include inducing expression of a homologous acyl-CoA synthase. The modified acyl-CoA biosynthetic pathway may include expressing a heterologous acyl-CoA thioesterase. The modified acyl-CoA biosynthetic pathway may include inducing expression of the heterologous acyl-CoA thioesterase. The modified acyl-CoA biosynthetic pathway may include mitigating degradation of the acyl-CoA. The heterologous acyl-CoA thioesterase may include a preference for myristoyl substrates. For example, the heterologous acyl-CoA thioesterase may be derived from *Cinnamomum camphorum*. The method may include inducing expression of the homologous acyl-CoA synthase, inducing expression of the heterologous acyl-CoA thioesterase, and mitigating degradation of the acyl-CoA.

In various embodiments, a N-acylated therapeutic peptide or protein is provided. The N-acylated therapeutic peptide or protein may be produced by fermentation of any aspect of the genetically modified microorganism as described herein. The N-acylated therapeutic peptide or protein may be produced by any of the methods described herein.

In some embodiments, the N-acylated therapeutic peptide or protein may include a N-acylated human peptide or protein. The N-acylated therapeutic peptide or protein may correspond to N-acylation of one of: somatotropin, glucagon, insulin, fibroblast growth factor 21, fibroblast growth factor 1, fibroblast growth factor 2, fibroblast growth factor 7, fibroblast growth factor 18, fibroblast growth factor 19, enkephalin, galanin, gastric inhibitory peptide, pancreatic prohormone, calcitonin, neuropeptide W, neuropeptide Y, hirudin, coagulation factor VIII, coagulation factor IX, tissue plasminogen activator, follicle-stimulating hormone, erythropoietin, granulocyte colony-stimulating factor, interferon, and asparaginase. The N-acylated therapeutic peptide or protein may correspond to N-acylation with one of a myristoyl group and a palmitoyl group.

In various embodiments, a gene or plasmid construct is provided. The gene or plasmid construct may include any gene or oligonucleotide described herein, or any gene or oligonucleotide for any protein, peptide, enzyme, tag, or other expression product described herein. The gene or plasmid construct may include, for example, one or more of: SEQ ID NO: 28, 30, 31, 32, 33, and 36.

Examples

The production of an exemplary genetically modified organism embodiment may now be described in the form of examples. While the embodiments may be described in considerable detail, it is not the intention to restrict or in any way limit the scope of the appended claims to such detail, or to any particular embodiment.

Materials & Methods

Unless otherwise stated, all materials and reagents were of the highest grade possible and purchased from Sigma (St. Louis, MO). Luria Broth was used for routine strain and plasmid propagation and construction. Working antibiotic concentrations were as follows: kanamycin (35 µg/mL), chloramphenicol (Cm 35 µg/mL), spectinomycin (Sp. 100 µg/mL), zeocin (Zeo. 50 µg/mL), gentamicin (Gent. 10 µg/mL), blasticidin (Bsd. 100 µg/mL), tetracycline (Tet. 5 µg/mL). Luria broth with low salt (Lennox formulation) was used to select for zeocin and blasticidin resistant clones.

Strain Construction

Chromosomal modifications were made using recombineering methodologies (Sharan, S. K.; Thomason, L. C.; Kuznetsov, S. G.; Court, D. L., Recombineering: a homologous recombination-based method of genetic engineering. *Nat Protoc* 2009, 4 (2), 206-23, the entire contents of which are incorporated herein by reference) either with direct antibiotic cassette integration or through scarless tet-sacB selection and counterselection, adapted from Li et al (Li, X. T.; Thomason, L. C.; Sawitzke, J. A.; Costantino, N.; Court, D. L., Positive and negative selection using the tetA-sacB cassette: recombineering and P1 transduction in *Escherichia coli*. *Nucleic Acids Res* 2013, 41 (22), e204, the entire contents of which are incorporated herein by reference). The recombineering plasmid pSIM5 and the tet-sacB selection/counterselection marker cassette were obtained from D. Court (NCI, //https://redrecombineering.ncifcrf.gov/courtlab.html//). Oligonucleotides and synthetic linear DNA used for strain construction (GBLOCKS™), given in Table 2, were obtained from Integrated DNA Technologies (IDT, Coralville, IA). Briefly, the tet-sacB selection/counterselection cassette was initially amplified with tetA_F (SEQ ID NO: 1) and sacB_R (SEQ ID NO: 2). Subsequently, PCR amplification using the appropriate oligos was performed to add ~50 bp flanking homology sequences to target specific genes (arsB known neutral site for chromosomal integration or ompT a membrane associated protease) using Econotaq (Lucigen Middleton, WI) according to manufacturer's instructions, with an initial 10 minutes denaturation at 94°, followed by 35 cycles of 94°, for 15 seconds, 52° for 15 seconds, and 72° for 5 minutes. Cassettes for "curing" the tet-sacB cassette and both simultaneous arsB deletion and integration of a low phosphate inducible his-tagged ulp1hydrolase (codon optimized for *E. coli*) or deletion of ompT were obtained as Gblocks™ from IDT. To change the native promoter of the gene fadD to the low phosphate inducible yibD gene promoter and replace the fadE to with Fatb I, synthetic linear DNA coding the desired chromosomal changes, along with ~50 bp of flanking homology sequences targeting fadD or fadE and an antibiotic cassette for direct selection (gentamicin for fadD and zeocin for fadE) were obtained as GBLOCKS™, and introduced by standard recombineering methods Chromosomal modifications were confirmed by PCR amplification and sequencing (Eton Biosciences) using paired oligonucleotides (SEQ ID NOs: 1-19), flanking the entire region.

Plasmid Cloning

The design and construction of plasmids as discussed above utilized the primers. Synthetic linear DNA coding hNMT-1 (including a N terminal His6 tag) and its peptide substrate (including the N terminal SUMO tag and the C terminal GST tag) were obtained as GBLOCKS™. These included ~20 bp flanking homology regions to clone them into expression vectors (pCDF for the enzyme and pSMART-HC for the substrate peptide) using NEBuilder® HiFi DNA Assembly Mix (New England Biolabs, Ipswich, MA) according to manufacturer's instructions. Briefly, pSMART-HC (Lucigen, Middleton, WI) was linearized using oligonucleotides SL1 (SEQ ID NO: 20) and SR2 (SEQ ID NO: 21) and Q5® High-Fidelity PCR Mix (New England Biolabs, Ipswich, MA), with an initial 2 minutes denaturation at 94°, followed by 35 cycles of 94° for 15 seconds, 60° for 15 seconds, and 72° for 1 minute. Similarly, pCDF was linearized in two pieces using as template a vector already containing the yibD gene promoter obtained from plasmid pCDF-mCherry (Addgene #65823). The PCR reactions used oligonucleotides sets pCDF_piece1_F/R (SEQ ID NOs: 22 and 23) and pCDF_piece2_F/R (SEQ ID NOs: 24 and 25), with an initial 2 minutes 30 seconds denaturation at 94°, followed by 35 cycles of 94° for 15 seconds, 59/63° for 15 seconds (piece 1/piece2), and 72° for 1 minute. The PCR products were gel purified using a DNA gel recovery kit (Zymo Research, Irvine, CA) and used together with 100 ng of the purchased GBLOCKS™ to perform a Gibson reaction for 15 minutes at 50°.

Further modifications to the plasmids were obtained using Q5@ High-Fidelity PCR Mix (New England Biolabs, Ipswich, MA). The N-terminal SUMO tag was removed from the peptide substrate to make pNAP-1-noSUMO using oligonucleotides remove SUMO_F/R (SEQ ID NOs: 18 and 19) with an initial 2 minutes 30 seconds denaturation at 94°, followed by 35 cycles of 94° for 15 seconds, 61° for 15 seconds, and 72° for 2 minutes and 30 seconds. The first N-terminal 80 amino acids of hNMT-1 were deleted from pCDF-His-hNMT-1 to make pCDF-yibD-delta80-His-hNMT-1 using oligonucleotides 80_hNMT-1_F/R (SEQ ID NOs: 26 and 27) with an initial 2 minutes 30 seconds denaturation at 94°, followed by 35 cycles of 94° for 15 seconds, 63° for 15 seconds, and 72° for 2 minutes and 30 seconds. The PCR products were gel purified using a DNA gel recovery kit (Zymo Research, Irvine, CA), and circularized during one hour at room temperature, using T4 DNA ligase in 1×T4 DNA ligase reaction buffer, in the presence of T4 polynucleotide kinase (3' phosphatase minus) and DpnI, all purchased from New England Biolabs, Ipswich, MA All plasmids sequences were confirmed by DNA sequencing (Eton Bioscience, NC) and deposited with Addgene.

TABLE 2

Microorganism Strains and Plasmids of the Examples

Plasmids

| Name | Genes | Addgene # | Source |
|---|---|---|---|
| pSMART-HC-Kan | ColE1, Kan, empty vector | — | Lucigen |
| pCDF-mCherry | CloDF13 origin, Sp, empty vector | 65823 | Ye, Z. et al, Nature Biotechnology (Submitted) 2017. |
| pCDF-hNMT-1 | CloDF13 origin, Sp, Δ80 human N-myristoyl transferase 1 | 87683 | This Study |
| pNAP-1 | ColE1, Kan, SUMO-GNAAAARR-GST | 87684 | This Study |
| pNAP-1-no SUMO | ColE1, Kan, M-GNAAAARR-GST | — | This Study |

Strains

| Name | Genotype | Plasmid(s) | Source |
|---|---|---|---|
| DLF_0025 | F-, λ-, Δ (araD-araB) 567, ΔlacZ4787, (::rrnB-3) rph-1, Δ (rhaD-rhaB) 568, hsdR514, BW25113, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB- pro-cas | | Ye, Z. et al, Nature Biotechnology (Submitted) 2017 |
| RLS_000 | DLF_025, ΔarsB::ugpBp-ULP1 | | This Study |
| RLS_001 | DLF_025, yibD-fadD | | This Study |
| RLS_002 | DLF_025, ΔfadE::CC-FatB1 | | This Study |
| RLS_003 | DLF_025, ΔfadE::CC-FatB1, yibD-fadD | | This Study |
| RLS_010 | RLS003, ΔompT | | This Study |
| RLS_011 | RLS000, ΔfadE::CC-FatB1, yibD-fadD | | This Study |

Shake Flask Experiments

Production of myristoyl-CoA, substrate peptides and hNMT-1 due to phosphate depletion was performed in vented cap square flasks (Genesee Scientific, San Diego, CA). Spectinomycin and/or kanamycin were added when appropriate. Cell cultures were started from frozen stocks in 50 ml (10 ml for myristoyl-CoA experiments) of Growth Medium One liter of Growth Medium consists of 9 g ammonium sulfate, 0.25 g citrate, 2.5 g yeast extract, 45 g glucose, 5 mM of phosphate buffer, 200 mM MOPS buffer (pH=7.4), 2.5 mM magnesium sulfate, 0.06 mM calcium sulfate, 10 mg thiamine-HCl, 0.16 mM iron(II) sulfate, supplemented with 0.2 ml of trace metals (for 1 liter of trace metals: 10 ml sulfuric acid, 0.6 g cobalt (II) sulfate heptahydrate, 5 g copper (II) sulfate pentahydrate, 0.6 g zinc sulfate heptahydrate, 0.2 g sodium molybdate dihydrate, 0.1 g boric acid and 0.3 g manganese (II) sulfate monohydrate), pH 6.8. The cultures were left to grow to 3 OD (600 nm) by incubating at 30° and 220 rpm overnight. Cells were induced by centrifuging and re-suspending them in Induction Medium (Growth Medium without phosphate or yeast extract); and incubating at 30° and 220 rpm Cells were harvested 24 hours after induction.

Analytical Methods

Myristoyl-CoA was extracted and quantified using conventional methods with some modifications as described below. Briefly, cells were pelleted by centrifugation and re-suspended in 0.5 ml of freshly made 100 mM potassium phosphate monobasic (pH 4.9) and 0.5 ml of acetonitrile:2-propanol:methanol (3:1:1). Cells were lysed using a Branson 4c15 sonicator (Branson Ultrasonics, Dansbury, CT) with 10 seconds, 30 seconds on/off cycles for 3 minutes at 50% tip amplitude. The cells were centrifuged at 14000 g and the supernatant was collected. The pellet was re-extracted using 0.5 ml of acetonitrile:2-propanol:methanol (3:1:1). After centrifuging again, the new supernatant was combined with the previous one and dried under nitrogen gas. The dried extract was resuspended in 200 ul of methanol:water (1:1). Myristoyl-CoA was separated using an Acquity UPLC (Waters Co, Milford, MA) in a Waters BEH C18 50 mm reverse phase column (Waters Co, Milford, MA). A gradient starting at 80% solvent A (15 mM NaOH in water) and 20% solvent B (15 mM NaOH in AcN) was used, and decreased it to 60% solvent A over 0.5 minutes, then decreased to 0% solvent A over 1 minute. The flow ran at 0% solvent A for 0.5 minutes, before turning back to the initial 80% solvent A gradient. The flow ran at 80% solvent A to re-equilibrate the column for the next sample for 1.5 minutes. Samples were detected using a Xevo TQD™ mass spectrometer (Waters Co, Milford, MA). A calibration curve was also performed using purchased myristoyl-CoA at 2, 1.6, 0.4, 0.1 and 0.025 mg/L. Extractions were performed in triplicates before and after phosphate induction. Values were normalized to biomass levels and always measured in the linear range of our calibration curve.

SDS-PAGE was performed using Mini-PROTEAN® TGX™ 4-20% gradient gels (Bio-rad, Hercules, CA). Samples were mixed 1:1 with 2× Laemmli sample buffer (Bio-rad, Hercules, CA). ~10 μg or ~500 ng of total protein were loaded for lysates or purified proteins respectively. Protein gels were stained using Coomassie Blue.

Myristoylation of the GNAAAARR tagged sequences was confirmed using matrix assisted laser desorption/ionization (MALDI) coupled with time of flight mass spectrometry using a Voyager DE (Applied Biosystems, Foster City, CA). Mass spectra were collected in positive ion mode using an acceleration voltage of 25 kV and a delay of 750 ns. Each mass spectrum collected represents the sum of 32 laser shots. Sinapinic acid was used as the matrix and aldolase was used as an internal standard. Data was calibrated and analyzed using the VOYAGER™ 5 software.

Analysis

With these chromosomal modifications and plasmid constructs as described above, a complete system for in vivo acylation of a target peptide or protein was obtained. In FIG. 1, production of acyl-CoAs was achieved through dynamic metabolic control upon phosphate medium depletion (a). AN-terminal SUMO tagged protein/peptide target was expressed (b) in an E. coli strain expressing the ulp1 hydrolase (c). The N-terminal SUMO tag was removed by ulp1 to expose the acylation recognition sequence (d).

Co-expression of hNMT-1 (e) resulted in the acyl group being transferred to the target protein/peptide (f).

In FIG. 3, heterologous *C. camphora* acyl-ACP thioesterase expression leads to increased myristic acid production by cleaving myristate from myristoyl-ACP and alleviating the inhibition of ACCase by acyl-ACPs (i). Overexpression of the fadD (acyl-CoA synthetase) by replacing its native promoter for the low phosphate inducible yibD gene promoter resulted in accumulation of myristoyl-CoA (ii). Deleting the fadE gene mitigated the beta oxidative pathway of acyl-CoAs, making them available for peptide lipidation (iii).

Figure 2:
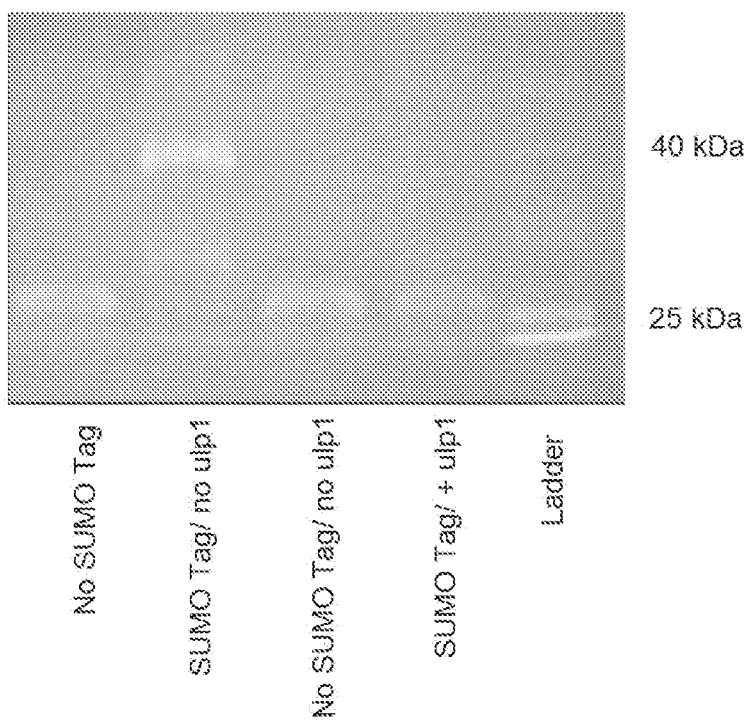
FIG. 2 is a SDS-PAGE of purified samples (C-terminally purified GST) expressed in strains with or without expression of ulp1 hydrolase and with or without a N-terminal SUMO-tag.

FIG. 2 is a SDS-PAGE of purified samples (C-terminally purified GST) expressed in strains with or without expression of ulp1 hydrolase and with or without a N-terminal SUMO-tag. FIG. 2 demonstrates in vivo expression and N-terminal SUMO tag cleavage by the ulp1 hydrolase.

Figure 4:
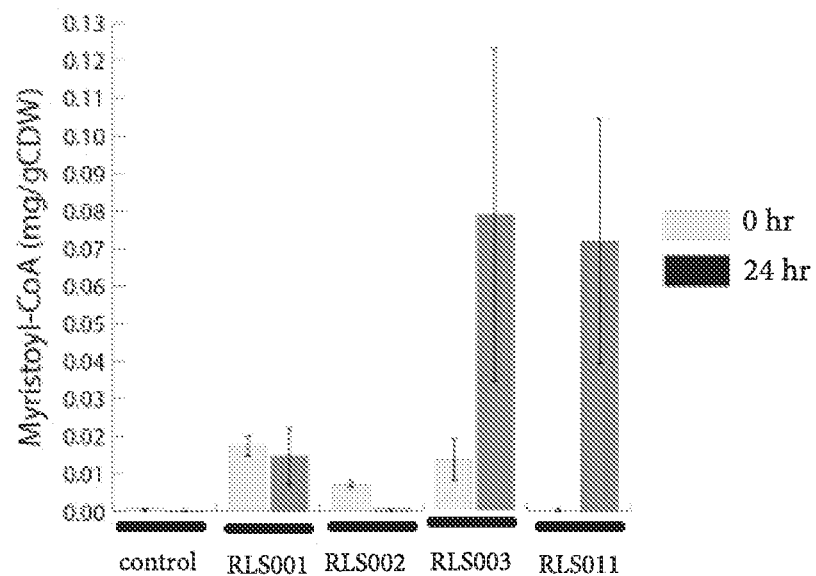
FIG. 4 shows improved Myristoyl-CoA (Myr-CoA) synthesis m genetically modified E. coli strains expressing an inducible thioesterase (TE), expressing an acyl CoA synthetase, and comprising mitigation of acyl CoA degradation before inductiongray) and 24 hours after induction (black).

FIG. 4 shows improved Myristoyl-CoA (Myr-CoA) synthesis in genetically modified *E. coli* strains expressing an inducible thioesterase (TE), expressing an acyl CoA synthetase, and comprising mitigation of acyl CoA degradation before inductiongray) and 24 hours after induction (black) .DLF25 was a control strain; RLS001 overexpressed the acyl-CoA synthetase; RLS002: fadE was deleted and the acyl-acp thioesterase was overexpressed (the thioesterase replaced fadE); RLS003: acylCoA was overexpressed, fadE was deleted, acyl-acp thioesterase was overexpressed. RLS11 acylCoA was overexpressed, fadE was deleted, acyl-acp thioesterase was overexpressed, ulp1 is present and the ompT gene was deleted. All strains were induced under low phosphate conditions to overexpress enzymes.

Figure 5:
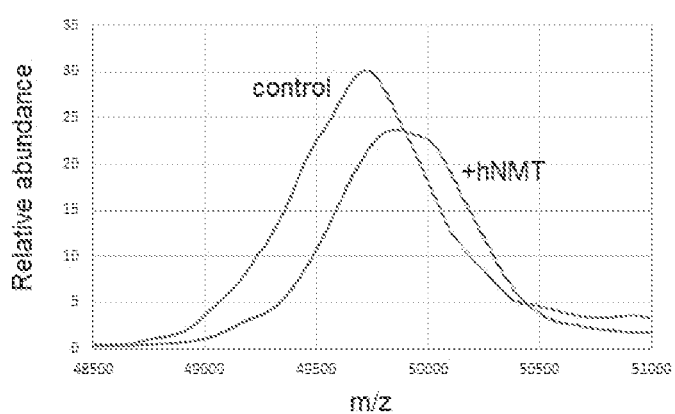
FIG. 5 depicts MALDI (matrix-assisted laser desorption/ionization) spectra of purified processed protein (SUMO tag cleaved) with or without co-expression of the hNMT (human N-myristoltransferase-1).

There are two bars per strain, before induction of acyl-CoA production (0 hr) and 24 hours after induction (24 hr). Control strains had minimal intracellular Myr-CoA. Overexpression of the fadD synthetase increased Myr-CoA pools. Deletion of fadE in combination with the overexpression of fadD and the TE lead to large increases in Myr-CoA. Pools were measured in cellular lysates 16 hrs post induction of the TE. The modifications of the microorganism as depicted in FIG. 3 lead to strain RLS_0011, which provided the biosynthesis and accumulation of myristoyl-CoA in vivo upon phosphate depletion. Introduction of plasmids pNAP-1 and pCDF-hNMT-1 into RLS_0011 provided the in vivo myristoylation of GNAAAARR-GST, which was confirmed by a shift in the center mass observed consistent with MALDI of purified proteins by −220 Da consistent with myristgoylation (FIG. 5).

Figure 6:
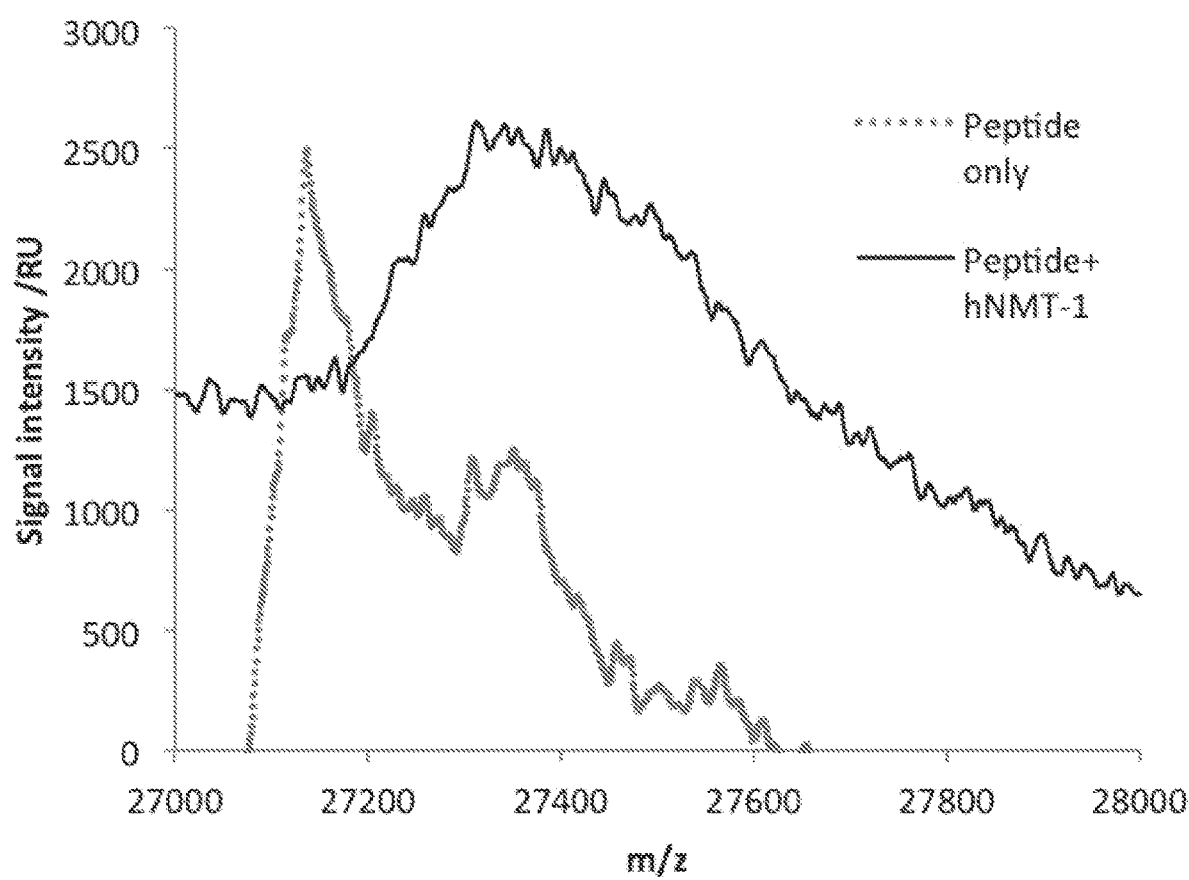
FIG. 6 depicts M depicts MALDI (matrix-assisted laser desorption/ionization) spectra of purified processed protein (SUMO tag cleaved) with or without co-expression of the hNMT (human N-myristoltransferase-1) on a single plasmid or construct.

FIG. 6 depicts M depicts MALDI (matrix-assisted laser desorption/ionization) spectra of purified processed protein (SUMO tag cleaved) with or without co-expression of the hNMT (human N-myristoltransferase-1). In this exemplary embodiment a single plasmid or construct for expressing both proteins (SEQ ID NO: 36) was expressed in a genetically modified microorganism that also contained a modified acyl-CoA biosynthetic pathway. As shown in FIG. 6, Accordingly, the genetically modified miroganism of the present invention co expresses at least two genes and, in some embodiments, up to five genes. In the Examples given above, individual contructs were used to introduce exogenous DNA into the genetically modified microorganism. However, the invention described herein may also encompass constructs, or exogenous DNA material that comprises more than one modified gene in a single unit. For example, SEQ ID NO: 37 encodes: amino acids 174-989: KanR (antibiotic resistance gene); 1052-1639: ori (origin of replication); 1725-2111: yibD promoter; 2130-3125: substrate protein (SUMO-substrate-GST); 3129-3418: phoB promoter; 447-4889: CBD-delta80 hNMT-1 (human myristoyl transferase 1 with the first 80 amino acids deleted and a chitin binding domain-CBD-fused to the N terminus.

One skilled in the art may readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses may occur to those skilled in the art which are encompassed within the spirit of the invention as defined by the scope of the claims.

Definitions

As used herein the terms "polypeptide", "peptide" and "protein" are used interchangeably to refer to a polymer of amino acid residues. The term percent (%) amino acid sequence identity between to amino acid polymer chains is defined as the percentage of amino acid residues identical between the chains when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences.

As used herein, a biomolecule that is heterologous in the context of the genetically modified microorganism, means that the heterologous biomolecule is not naturally found in an unmodified microorganism form which the genetically modified microorganism was derived. For example, in *E. coli*, genetically modified to express a human protein from a human gene, both the human protein and human gene in the genetically modified *E. coli* are heterologous compared to unmodified *E. coli*. The phrase or term native refers to naturally occurring or homologous indicating it would be found in an unmodified *E. coli*.

The terms lipidation, fatty acylation, acylation are all used in this specification to refer to the transfer of a fatty acid having a chain length of about C8-C18 from a fatty acyl-CoA to a peptide or protein thus resulting in an acylated, fatty acylated and lipidated protein.

Fatty acids that are saturated, monounsaturated or polyunsaturated may be used for protein N-acylation. Preferably the fatty acids contain between 8 and 18 carbons, although fatty acyl groups with between 2 and 26 carbons are encompassed. Acyl Co—As containing fatty acids known as: butanoic acid, hexanoic acid, octanoic acid, decanoic acid, dodecanoic acid, tridecnoic acid, tetradecanoic acid, pentadecanoic acid, hexadecanoic acid, heptadecanoic acid, octadecanoic, nonadecanoic acid, eicosanoic acid, docosanoic acid, tetracosanoic acid, butyric acid, caproic acid, caprylic acid, capric acid, lauric acid, myristic acid, palmitica acid, margaric acid, stearic acid, arachidic acid, behenic acid, lignoceric acid, tetradecenoic acid, myristoleic acid, myristol, palmitolyl, palmitoleic acid, hesadecenoic acid, pentadecenoic acid, heptadecenoic acid, octadecenoic acid, oleic acid, gadoleic acid, eicosenoic acid, erucic acid, docosenoic acid, nervonic acid, hexadecadienoic acid, octadecadienoic acid, linoleic acid, linolenic acid, octadecatrienoic acid, octadecatetraenoic acid, parinaric acid, gamma-linolenic acid, alpha-linolenic acid, arachidonic acid, timnodonic acid, brassic acid, clupanodonic acid, eicosadienoic acid, eicosatrienoic acid, eicosatetraenoic acid, eicosapentaenoic acid (EPA), docosapentaenoic acid (DPA), docosahexaenoic acid (DHA) may be used for protein N-acylation.

Although some of the genetic modifications of a genetically modified organism are described as occurring in a bacterial strain and particularly *E. coli* in the examples, it may be appreciated that the same genetic modification may be made any host microorganism including any prokaryotic and eukaryotic host microorganism. Some modifications of the genetically modified microorganism occur on exogenous vectors or plasmids. A plasmid as used herein may also be referred to as a vector or exogenous DNA. It may be appreciated that the same genetic modification may also occur by modification of the chromosome of the host microorganism.

To the extent that the term "includes" or "including" is used in the specification or the claims, it is intended to be inclusive in a manner similar to the term "comprising" as that term is interpreted when employed as a transitional word in a claim Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive, and not the exclusive use. As used in the specification and the claims, the singular forms "a," "an," and "the" include the plural. Finally, where the term "about" is used in conjunction with a number, it is intended to include 10% of the number. For example, "about 10" may mean from 9 to 11. The term wt % is meant to describe a comparison of the weight of one compound to the weight of the whole composition expressed as a percent. It can also be described as wt. %, or (w/w) %. As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept.

The invention claimed is:

1. A method of in vivo acylation of a target peptide or protein in an *E. coli* microorganism strain, comprising:

providing an *E. coli* microorganism strain expressing a first gene that encodes a human N-myristol transferase and expressing a second gene that encodes a target peptide or protein to be N-acylated operatively linked to an oligonucleotide encoding a substrate for the acyl transferase, the *E. coli* microorganism strain having chromosomal modifications resulting in a genotype comprising ΔfadE::CC-FatBI, yibD-fadD so that, compared to a native acyl-CoA biosynthetic pathway in the native microorganism, the *E. coli* microorganism strain is configured for inducible expression or overexpression of an endogenous fadD gene and a thioesterase gene upon depletion of phosphate from fermentation medium, fermenting the microorganism under condition effective to cause acylation of the target peptide or protein by the human N-myristol transferase to provide a N-acylated peptide or protein product.

2. The method of claim 1, wherein the *E. coli* microorganism further comprises inducible production of the human N-myristol transferase or the peptide or protein encoded by the second gene.

3. The method of claim 1, wherein the *E. coli* microorganism further comprises a phosphate-regulated promoter that is yibD or ugpB, operatively linked to one or more of: the first or second gene.

4. The method of claim 1, wherein the *E. coli* microorganism comprises a mutation in an acyl-CoA binding site of the first gene that alters the acyl-CoA substrate specificity of the acyl transferase.

5. The method of claim 1, comprising expressing the second gene encoding one of: somatotropin, glucagon, insulin, fibroblast growth factor 21, fibroblast growth factor 1, fibroblast growth factor 2, fibroblast growth factor 7, fibroblast growth factor 18, fibroblast growth factor 19, enkephalin, galanin, gastric inhibitory peptide, pancreatic prohormone, calcitonin, neuropeptide W, neuropeptide Y, hirudin, coagulation factor VIII, coagulation factor IX, tissue plasminogen activator, follicle-stimulating hormone, erythropoietin, granulocyte colony-stimulating factor, interferon, and asparaginase.

6. The method of claim 1, wherein the *E. coli* microorganism further comprises:

a first oligonucleotide that encodes a protein tag, the first oligonucleotide operatively linked to the second gene so that expression using the first oligonucleotide and the second gene results in a product comprising the protein tag operatively linked to the N-terminus of the peptide or protein; and a third gene that encodes a cleaving enzyme configured to cleave the protein tag from the peptide or protein, the third gene including one of: ulp1, enterokinase, a TEV (tobacco etch virus), a thrombin or PreScission or other substrate specific protease.

7. The method of claim 1, wherein the *E. coli* microorganism further comprises a second oligonucleotide that encodes a C-terminal tag, the second oligonucleotide operatively linked to the second gene so that expression using the second oligonucleotide and the second gene results in a product comprising the C-terminal tag and the peptide or protein, the C-terminal tag being one of: a glutathione S-transferase, a maltose binding protein, a calmodulin binding peptide, a his-patch thiofusion, a tap affinity purification tag, an epitope tag, a reporter tag, a modified haloalkane dehalogenase, SUMO, a serine proteinase, a post-synaptic density protein, a streptavidin/biotin-based tag, a chitin binding domain tag, and a polyhistidine.

8. The method of claim 1, wherein the *E. coli* microorganism further comprises: a third oligonucleotide that encodes a substrate, the third oligonucleotide operatively linked to the first oligonucleotide and the second gene so that expression using the first oligonucleotide, the third oligonucleotide, and the second gene produces a product comprising the protein tags, the substrate, and the peptide or protein.

9. The method of claim 8, wherein the substrate is a substrate for a glycylpeptide N-tetradecanoyltransferase.

10. The method of claim 1, wherein the *E. coli* microorganism further comprises:
- a fourth oligonucleotide that encodes a methionine aminopeptidase sensitive protease tag, the fourth oligonucleotide being operatively linked to the second gene so that expression using the fourth oligonucleotide and the second gene produces a product comprising the methionine aminopeptidase sensitive protease tag operatively linked to the N-terminus of the peptide or protein; and
- a third gene that encodes a cleaving enzyme configured to cleave the methionine aminopeptidase sensitive protease tag from the peptide or protein.

11. The method of claim 1, further comprising: expressing a substrate operatively linked between the protein tag and the peptide or protein to produce a product comprising the protein tags, the substrate, and the peptide or protein.

12. The method of claim 1, wherein the modified acyl-CoA biosynthetic pathway being configured to induce expression of a homologous acyl-CoA synthase and mitigate degradation of the acyl-CoA by deletion of a fade gene.

13. The method of claim 1, wherein the *E. coli* microorganism is further configured to induce expression of the homologous acyl-CoA synthase, express the heterologous acyl-CoA thioesterase, and mitigate degradation of the acyl-CoA.

14. The method of claim 1, comprising synthesizing the acyl-CoA using the modified acyl-CoA biosynthetic pathway comprising one or more of:
- inducing expression of a homologous acyl-CoA synthase encoded by a fourth gene;
- expressing a heterologous acyl-CoA thioesterase, from *Cinnamomum camphorum*, encoded by a fifth gene;
- inducing expression of the heterologous acyl-CoA thioesterase; and
- mitigating degradation of the acyl-CoA by deletion of a sixth gene,
- the modified acyl-CoA biosynthetic pathway comprising deletion of a gene encoding fadE.

* * * * *

```
                      SEQUENCE LISTING

<160> NUMBER OF SEQ ID NOS: 37

<210> SEQ ID NO 1
<211> LENGTH: 25
<212> TYPE: DNA
<213> ORGANISM: Artificial Sequence
<220> FEATURE:
<223> OTHER INFORMATION: Synthetic

<400> SEQUENCE: 1
tcctaatttt tgttgacact ctatc                                         25

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
atcaaaggga aaactgtcca tatgc                                         25

<210> SEQ ID NO 3
<211> LENGTH: 74
<212> TYPE: DNA
<213> ORGANISM: Artificial Sequence
<220> FEATURE:
<223> OTHER INFORMATION: Synthetic

<400> SEQUENCE: 3
caaatgaata gccaactcaa aattcacacc tattccttc ctctgcactt cctaattttt    60
gttgacactc tatc                                                    74

<210> SEQ ID NO 4
<211> LENGTH: 72
<212> TYPE: DNA
<213> ORGANISM: Artificial Sequence
<220> FEATURE:
<223> OTHER INFORMATION: Synthetic

<400> SEQUENCE: 4
aaataaagcg cacttttcta acaacctgtg gggggggatat cgccgctatc aaagggaaaa  60
```

```
ctgtccatat gc                                                        72

<210> SEQ ID NO 5
<211> LENGTH: 77
<212> TYPE: DNA
<213> ORGANISM: Artificial Sequence
<220> FEATURE:
<223> OTHER INFORMATION: Synthetic

<400> SEQUENCE: 5
agatataaaa aatacatatt caatcattaa aacgattgaa tggagaactt tttcctaatt    60
tttgttgaca ctctatc                                                   77

<210> SEQ ID NO 6
<211> LENGTH: 78
<212> TYPE: DNA
<213> ORGANISM: Artificial Sequence
<220> FEATURE:
<223> OTHER INFORMATION: Synthetic

<400> SEQUENCE: 6
gaaatggcta gttattcccc ggggcgattt tcacctcggg gaaattttag ttgatcaaag    60
ggaaaactgt ccatatgc                                                  78

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
aacggataag acgggcataa at                                             22

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8
agattaaggg atgaaggaac gtc                                            23

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
atttccgtgg acaactggtt a                                              21

<210> SEQ ID NO 10
<211> LENGTH: 18
<212> TYPE: DNA
<213> ORGANISM: Artificial Sequence
<220> FEATURE:
<223> OTHER INFORMATION: Synthetic

<400> SEQUENCE: 10
ggacggcttc acacaaag                                                  18
```

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
aactgaataa ttgcttgttt tt                                          22

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
gctcaaacat atctaccaga ga                                          22

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
atgactaacg tcagaaatag c                                           21

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
cgggaggaat gatgtttaag                                             20

<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15
atgtttttac atccactaca acc                                         23

<210> SEQ ID NO 16
<211> LENGTH: 19
<212> TYPE: DNA
<213> ORGANISM: Artificial Sequence
<220> FEATURE:
<223> OTHER INFORMATION: Synthetic

<400> SEQUENCE: 16
atccggatgg ctttaattt                                              19

<210> SEQ ID NO 17
<211> LENGTH: 19
<212> TYPE: DNA
<213> ORGANISM: Artificial Sequence
<220> FEATURE:
<223> OTHER INFORMATION: Synthetic

```
<400> SEQUENCE: 17
atgggtacgt ttgaccacc                                                    19

<210> SEQ ID NO 18
<211> LENGTH: 15
<212> TYPE: DNA
<213> ORGANISM: Artificial Sequence
<220> FEATURE:
<223> OTHER INFORMATION: Synthetic

<400> SEQUENCE: 18
gggaacgcag cagct                                                        15

<210> SEQ ID NO 19
<211> LENGTH: 39
<212> TYPE: DNA
<213> ORGANISM: Artificial Sequence
<220> FEATURE:
<223> OTHER INFORMATION: Synthetic

<400> SEQUENCE: 19
cattatatcc tccttaatag tattttataa aagttaaac                              39

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
cagtccagtt acgctggagt c                                                 21

<210> SEQ ID NO 21
<211> LENGTH: 26
<212> TYPE: DNA
<213> ORGANISM: Artificial Sequence
<220> FEATURE:
<223> OTHER INFORMATION: Synthetic

<400> SEQUENCE: 21
ggtcaggtat gatttaaatg gtcagt                                            26

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
gacgaattct ctagatatcg c                                                 21

<210> SEQ ID NO 23
<211> LENGTH: 18
<212> TYPE: DNA
<213> ORGANISM: Artificial Sequence
<220> FEATURE:
<223> OTHER INFORMATION: Synthetic

<400> SEQUENCE: 23
gcaggtatct tcgagcca                                                     18

<210> SEQ ID NO 24
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 24
tggctcgaag atacctgc                                                 18

<210> SEQ ID NO 25
<211> LENGTH: 18
<212> TYPE: DNA
<213> ORGANISM: Artificial Sequence
<220> FEATURE:
<223> OTHER INFORMATION: Synthetic

<400> SEQUENCE: 25
ggaaaccgtt gtggtctc                                                 18

<210> SEQ ID NO 26
<211> LENGTH: 18
<212> TYPE: DNA
<213> ORGANISM: Artificial Sequence
<220> FEATURE:
<223> OTHER INFORMATION: Synthetic

<400> SEQUENCE: 26
aactcgttgc ctgctgag                                                 18

<210> SEQ ID NO 27
<211> LENGTH: 21
<212> TYPE: DNA
<213> ORGANISM: Artificial Sequence
<220> FEATURE:
<223> OTHER INFORMATION: Synthetic

<400> SEQUENCE: 27
gtgatggtga tggtgatgca t                                             21

<210> SEQ ID NO 28
<211> LENGTH: 1243
<212> TYPE: DNA
<213> ORGANISM: Artificial Sequence
<220> FEATURE:
<223> OTHER INFORMATION: Synthetic

<400> SEQUENCE: 28
ccaggcatca ataaaaacga aaggctcagt cgaaagactg ggcctttcgt tttatctgtt    60
gtttgtcggt gaacgctctc tactagagtc acactggctc accttcgggt gggcctttct   120
gcgtttatac acagctaaca ccacgtcgtc cctatctgct gccctaggtc tatgagtggt   180
tgctggataa ctctttctga caccttacta tcttacaaat gtaacaaaaa agttattttt   240
ctgtaattcg agcatgtcat gttaccccgc gagcataaaa cgcgtatatt cagggagacc   300
acaacggttt ccctctacaa ataatttttgt ttaactttga attcaaaaga tctggtacca   360
cctttaagaa ggagatatac atatgcgggg ttctcatcac catcatcacc atggtctggt   420
tccgcgtgga tcccttgttc ctgaattaaa tgaaaaagac gatgaccaag tacaaaaagc   480
tttggcatct agagaaaata ctcagttaat gaatagagat aatatagaga taacagtacg   540 tgatttttaag accttggcac cacgaagatg gctaaatgac actatcattg agtttttttat   600 gaaatacatt gaaaaatcta ccccctaatac agtggcgttt aattcgtttt tctataccaa   660
tttatcagaa aggggttatc aaggcgtccg gaggtggatg aagagaaaga agacacaaat   720
```

| | |
|---|---|
| tgataaactt gataaaatct ttacaccaat aaatttgaac caatcccact gggcgttggg | 780 |
| cataattgat ttaaaaaga aaactatagg ttacgtagat tcattatcga atggtccaaa | 840 |
| tgctatgagt ttcgctatac tgactgactt gcaaaaatat gttatggagg aaagtaagca | 900 |
| tacaatagga gaagactttg atttgattca tttagattgt ccgcagcaac caaatggcta | 960 |
| cgactgtgga atatatgttt gtatgaatac tctctatgga agtgcagatg cgccattgga | 1020 |
| ttttgattat aaagatgcga ttaggatgag aagatttatt gcccatttga ttttaaccga | 1080 |
| cgctttaaaa taagaattcg aagcttgatc cggctgctaa caaagcccga aggaagctg | 1140 |
| agttggctgc tgccaccgct gagcaataac tagcataacc ccttgggcc tctaaacggg | 1200 |
| tcttgagggg ttttttgctg aaaggaggaa ctatatccgg atc | 1243 |

<210> SEQ ID NO 29
<211> LENGTH: 749
<212> TYPE: DNA
<213> ORGANISM: Artificial Sequence
<220> FEATURE:
<223> OTHER INFORMATION: Synthetic

<400> SEQUENCE: 29

| | |
|---|---|
| ccgcgacagc gtctgccgca ttattcaaag cgatattcag cattactgga atctgcgaat | 60 |
| tgtcgccagt tcgctatgtt taagccccag cctgctcaaa aagaaattaa aaaacgaaaa | 120 |
| taccagctat agccagattg tcacagagtg tcgtatgcgt tacgccgtac agatgttatt | 180 |
| gatggataac aaaaatatca ctcaggtggc gcaattatgt ggctatagca gcacgtcgta | 240 |
| cttatctct gttttaagg cgttttacgg cctgacaccg ttgaattatc tcgccaaaca | 300 |
| gcgacaaaaa gtgatgtggt gaagggcaaa gcggaaacgg ataagacggg cataaatgag | 360 |
| gaagaaatgg cgcgccctgc gaacgccaac taaaatttcc ccgaggtgaa atcgccccg | 420 |
| gggaataact agccatttca atgtaacaat taaccttaa aataaaccca gaaggttatt | 480 |
| aactaaatca catagaaaac catcaattat agtatgtata aataggcga cagcaaccca | 540 |
| attacaaatt aatggttcca gaatatcaca tcaaaaaaaa cgctgtataa tattataatt | 600 |
| aacatgtaga caacttgtaa taaacattat cagtcaattg ttttgtttat tccatctgtg | 660 |
| acgccgatta ttttctcaaa ataatgagat ggcgtgacac cataataatc tttaaatgca | 720 |
| catatgaaat atgaagtact gttatagcc | 749 |

<210> SEQ ID NO 30
<211> LENGTH: 1223
<212> TYPE: DNA
<213> ORGANISM: Artificial Sequence
<220> FEATURE:
<223> OTHER INFORMATION: Synthetic

<400> SEQUENCE: 30

| | |
|---|---|
| aactgaataa ttgcttgttt ttaaagaaaa agaaacagcg gctggtccgc tgtttctgca | 60 |
| ttcttacggt aaagataaaa ataaatagtg acgcgcttcg cgaatccatg tgggagttta | 120 |
| ttcttgacac agatatttat gatataataa ctgagtaagc ttaacataag gaggaaaaac | 180 |
| atatgttacg cagcagcaac gatgttacgc agcagggcag tcgccctaaa acaaagttag | 240 |
| gtggctcaag tatgggcatc attcgcacat gtaggctcgg ccctgaccaa gtcaaatcca | 300 |
| tgcgggctgc tcttgatctt ttcggtcgtg agttcggaga cgtagccacc tactcccaac | 360 |
| atcagccgga ctccgattac ctcgggaact tgctccgtag taagacattc atcgcgcttg | 420 |

```
ctgccttcga ccaagaagcg gttgttggcg ctctcgcggc ttacgttctg cccaagtttg      480
agcagccgcg tagtgagatc tatatctatg atctcgcagt ctccggcgag caccggaggc      540
agggcattgc caccgcgctc atcaatctcc tcaagcatga ggccaacgcg cttggtgctt      600
atgtgatcta cgtgcaagca gattacggtg acgatcccgc agtggctctc tatacaaagt      660
tgggcatacg ggaagaagtg atgcactttg atatcgaccc aagtaccgcc acctatgccc      720
aggcatcaaa taaaacgaaa ggctcagtcg aaagactggg cctttcgttt tatctgttgt      780
ttgtcggtga acgctctcta ctagagtcac actggctcac cttcgggtgg ccttttctgc      840
gtttatacac agctaacacc acgtcgtccc tatctgctgc cctaggtcta tgagtggttg      900
ctggataacg tgcgtaattg tgctgatctc ttatatagct gctctcatta tctctctacc      960
ctgaagtgac tctctcacct gtaaaaataa tatctcacag gcttaatagt ttcttaatac     1020
aaagcctgta aaacgtcagg ataacttcta tattcaggga gaccacaacg gtttccctct     1080
acaaataatt ttgtttaact ttcgtaaaga ggagaaatac tagttgaaga aggtttggct     1140
taaccgttat cccgcggacg ttccgacgga gatcaaccct gaccgttatc aatctctggt     1200
agatatgttt gagcagtcgg tcg                                             1223

<210> SEQ ID NO 31
<211> LENGTH: 2018
<212> TYPE: DNA
<213> ORGANISM: Artificial Sequence
<220> FEATURE:
<223> OTHER INFORMATION: Synthetic

<400> SEQUENCE: 31 atgttttac atccactaca accatatcat cacaagtggt cagacctcct acaagtaagg       60
ggcttttcgt tttactaaac tgaactttct gccggaatga cgctgatgcc acgaaagcta     120
tcggtaagtt tcggacgcca ttcggtctta gcgcgcagca cttcgctacc tccttccagc     180
tgcagcagat gttcgcaaac cagacctgct tcactgctac cgcccgatac cgtcgtcagg     240
ctctgtaaca cactatccat ggtacattca cgacgatatt cgatggtaaa gctactgata     300
tgatggcttt cgaagatgct atctggcacg gtttccagaa tccagtcaac gtatttgatg     360
ttgttgacat gttggttgat gtccaaatca ttccagcgcg gggtaagtcc cccttggata     420
taatcggcgg tgctatcgtt caatttctgc ggttttttaa tttcctcatc tttcacggcc     480
acgttgtcaa tgaaagccgg gccaatttca ccacgcactt cctccgggat tttagacaga     540
cgacgggtac gagtgttcat cataacgctc aggctcgtgc agcgggtcag aatctccccc     600
gttttgcaat cacgcactaa gaaatcgtga cgacgcccgt tattgccgga cgcccctacc     660
caacactcca cttcaactgt gtcgccccat gccggatagc gctccacggc aacatgggta     720
cgtttgacca cccaaataag atcacgctta gacatttcta acgtggtgcc aaaaccatct     780
cccaggatac caacagattt ggcatggttg agtgccgcct cctgtaagtg gttcatgact     840
gccacgatgc tagtactacg gtctgggccc acttcataag aacggatggc gaaggtgcgg     900
cggaacacca gaccatgcgg accgaaatgg tcgtccagga gctgtggcgg atttggtttg     960
ggtttccact ccagattcgt ccactgcttt tccgccgcac taaaaatggt agtgataacc    1020
gcgaataaca tgctccaatc cggcagtttt ttaagggatt cggtgtagct aaatttggta    1080
ccgttgatca ttttcaggct ggtctgtgca ttgccggcac gtaactgtaa gtcagagcta    1140
cgcggtttca tcccacgtcc atcgcgagcc agcataactg ctttcatcga acaaaaagcg    1200
ctcgccaggg atgtggttgc catctagtat ttctcctctt tacgaaagtt aaacaaaatt    1260
```

```
atttgtagag ggaaaccgtt gtggtctccc tgaatataga agttatcctg acgttttaca      1320
ggctttgtat taagaaacta ttaagcctgt gagatattat ttttacaggt gagagagtca      1380
cttcagggta gagagataat gagagcagct atataagaga tcagcacaat tacgcacgtt      1440
atccagcaac cactcataga cctagggcag cagatatagga cgacgtggtg ttagctgtgt     1500
tgacaattaa tcatcggcat agtatatcgg catagtataa tacgactcac tataggaggg     1560
ccatcatggc caagttgacc agtgccgttc cggtgctcac cgcgcgcgac gtcgccggag     1620
cggtcgagtt ctggaccgac cggctcgggt tctcccggga cttcgtggag gacgacttcg     1680
ccggtgtggt ccgggacgac gtgaccctgt tcatcagcgc ggtccaggac caggtggtgc     1740
cggacaacac cctggcctgg gtgtgggtgc gcggcctgga cgagctgtac gccgagtggt     1800
cggaggtcgt gtccacgaac ttccgggacg cctccgggcc ggccatgacc gagatcggcg     1860
agcagccgtg ggggcgggag ttcgccctgc gcgacccggc cggcaactgc gtgcactttg     1920
tggcagagga gcaggactga ggataagata acggagccga aaggctccgt ttctttatcc     1980
gctaattatt taaaattaaa gccatccgga tggttttc                             2018

<210> SEQ ID NO 32
<211> LENGTH: 1598
<212> TYPE: DNA
<213> ORGANISM: Artificial Sequence
<220> FEATURE:
<223> OTHER INFORMATION: Synthetic

<400> SEQUENCE: 32
gagaccacaa cggtttccct ctacaaataa ttttgtttaa ctttaaagag gagaaatact       60
agatgcatca ccatcaccat cacatggcag atgaatcgga aaccgcggtt aaaccgccgg      120
cgccgcccct tccgcagatg atggaaggta acggcaatgg gcatgagcat tgcagcgact      180
gcgaaaacga ggaagataat tcgtataatc gtggtggact gtccccagcg aacgataccg      240
gtgcaaaaaa aagaagaaa aagcagaaaa agaaaaaaga gaaaggcagc gaaaccgata      300
gcgctcaaga tcagccagtg aaaatgaact cgttgcctgc tgagcgtatc caagaaattc      360
agaaggcaat tgaactgttt agcgtgggtc aaggcccagc caaaacgatg gaggaagcga      420
gcaaacgttc gtatcagttc tgggatacgc aaccggtgcc gaagctcggt gaagtggtga      480
atacgcacgg gcctgttgag ccggataagg acaatattcg tcaggagcca tatacgctgc      540
ctcagggttt cacttgggac gccctggacc tgggtgaccg tggtgtgctg aaagaactgt      600
acaccctgct taatgagaat tatgtagaag atgacgacaa catgttccgt tttgactata      660
gcccggaatt cctgttatgg gcactccgtc cgccggggttg gctgccgcag tggcattgcg     720
gtgtccgcgt agtttcgagc cgtaaactcg taggtttcat cagtgcaatc ccggccaaca     780
ttcatatcta tgacaccgag aaaaaaatgg tagaaattaa cttcctgtgt gttcataaga     840
agttgcgtag caaacgcgta gcgcctgtcc tcattcgtga aatcacgcgc gcgtacatt     900 tagaaggtat cttccaggca gtatatactg ctggcgtcgt gctcccaaaa ccggttggga     960
cttgccgcta ttggcaccgc tctctgaatc cgcgtaagct gattgaagtt aaatttagcc     1020
atttgtcacg caacatgacc atgcagcgca ccatgaaact ttaccgtctg ccggaaaccc     1080
cgaaaactgc tggtttgcgc ccaatggaga cgaaagatat tcctgtcgtc catcagctgc     1140
tgacgcgtta tttaaaacag tttcacttaa ctcctgtcat gagccaggaa gaggttgaac     1200
attggtttta tccgcaagaa aacatcatcg acaccttcgt agtggagaat gcgaatggcg     1260
```

| | |
|---|---|
| aagtcacgga cttttttatcc ttctatactt tgccgagcac catcatgaac catccgaccc | 1320 |
| ataaaagcct gaaggccgcg tactcatttt ataatgtcca cacgcagacc ccgttattgg | 1380 |
| atctgatgtc tgatgcgttg gtcctggcca aaatgaaagg tttcgacgtt tttaatgcgc | 1440 |
| tggacctgat ggagaacaaa acctttctgg aaaaattgaa attcggaatt ggcgatggta | 1500 |
| atctgcaata ctatctgtat aattggaaat gcccgtcgat gggtgcggaa aaagttggtc | 1560 |
| tggtactgca gtagtaagac gaattctcta gatatcgc | 1598 |

<210> SEQ ID NO 33
<211> LENGTH: 2095
<212> TYPE: DNA
<213> ORGANISM: Artificial Sequence
<220> FEATURE:
<223> OTHER INFORMATION: Synthetic

<400> SEQUENCE: 33

| | |
|---|---|
| cagtccagtt acgctggagt ctgcccaggc atcaaataaa acgaaaggct cagtcgaaag | 60 |
| actgggcctt tcgttttatc tgttgtttgt cggtgaacgc tctctactag agtcacactg | 120 |
| gctcaccttc gggtgggcct ttctgcgttt atacacagct aacaccacgt cgtccctatc | 180 |
| tgctgcccta ggtctatgag tggttgctgg ataacgtgcg taattgtgct gatctcttat | 240 |
| atagctgctc tcattatctc tctaccctga agtgactctc tcacctgtaa aaataatatc | 300 |
| tcacaggctt aatagtttct aatacaaag cctgtaaaac gtcaggataa cttctatatt | 360 |
| cagggagacc acaacggttt ccctctacaa ataattttgt ttaactttta taaaatacta | 420 |
| ttaaggagga tataatgtcg acagtgaag tcaaccagga agcgaaaccg gaagtgaaac | 480 |
| cggaagtcaa acctgaaacg cacattaatc tgaaagtcag cgatggttcc agtgaaatct | 540 |
| tcttcaaaat taaaaaaact acgccgttac gtcgtttgat ggaagcattt gcgaaacgcc | 600 |
| agggcaagga aatggattcc ctccgcttct tatatgacgg gattcgtatc caagcagacc | 660 |
| aaaccccgga ggacctggac atggaagaca acgatattat tgaagcacat cgcgaacaga | 720 |
| ttgggggcgg gaacgcagca gctgcgcgtc gccgtcgccg ctgcattacg ggggatgcac | 780 |
| tggtcgcatt gcctgagggt gagagtgtgc gtattgcgga cattgtccct ggcgcgcgcc | 840 |
| ccaactccga taacgcaatc gatctgaagg tcctggaccg ccacggcaat cccgtattag | 900 |
| cagatcgttt attccattcg ggagaacatc cagtgtacac agtacgtact gtggaaggat | 960 |
| tacgtgtcac cggaactgca atcatccgc tgttgtgctt ggtagatgtt gcaggagtgc | 1020 |
| ctacactgtt gtggaaactg atcgacgaga tcaaaccagg cgattacgct gtaatccagc | 1080 |
| gtagtgcgtt ttcggtggac tgcgcgggtt ttgcgcgtgg caaacctgag ttcgccccta | 1140 |
| cgacttatac tgttggagtg cctggtctgg tccgtttttt agaagctcac catcgcgacc | 1200 |
| cagacgctca ggccatcgct gatgagttga cagacggtcg cttctattac gcaaaggtag | 1260 |
| cgagtgtaac agacgcaggg gtgcaacctg tctacagttt gcgtgttgac acagcggacc | 1320 |
| acgcatttat caccaatggc ttcgtctcgc atgcgacggg attgaccggg cttaactctg | 1380 |
| gattgactga aaatctctat tttcagggca tgtccccgat cctgggttac tggaaaatca | 1440 |
| aagggttagt gcagccaacc cgtctgttat tagaatacct ggaggaaaaa tacgaggaac | 1500 |
| acctgtacga gcgcgatgaa ggcgataaat ggcgcaataa aaaattcgaa ctcgggctgg | 1560 |
| aattcccaaa cttaccctat tatattgatg gagatgttaa attgacccag tctatggcaa | 1620 |
| tcattcgcta tattgcagat aaacataaca tgttgggcgg ctgtcctaag gagcgcgcg | 1680 |
| aaattagtat gctggaaggc gcggtgctgg atatccgcta tggtgttagc cgcattgcgt | 1740 |

```
actcgaaaga ttttgagacg ctcaaagttg attttctgag taaactgcct gaaatgttaa   1800
agatgtttga agatcgcttg tgtcacaaaa cgtatttaaa tggtgatcat gtcacccatc   1860
cagactttat gctgtatgat gcgcttgatg tggttttgta catggatccg atgtgcctgg   1920
atgcctttcc gaagctggtc tgtttcaaaa acgcatcga ggctattccg caaatcgaca    1980
aatatctcaa atctagtaaa tacatcgcgt ggcctctgca gggctggcaa gcgacctttg   2040 gtggggcga tcatccgcca aaataatgaa ctgaccattt aaatcatacc tgacc         2095
```

<210> SEQ ID NO 34
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: human-myristoyl transferase-1 recognition substrate
<222> LOCATION: (1)..(8)
<223> OTHER INFORMATION: peptides with the sequence X1X2X3X4X5X6X7X8
       where X1 is glycine, X2 and X5 are small uncharged residues, but
       proline; X6 is any residue but proline and X3, X4, X7 and X8 are
       any residues

<400> SEQUENCE: 34

Xaa Xaa Xaa Xaa Xaa Xaa Xaa Xaa
1               5

<210> SEQ ID NO 35
<211> LENGTH: 98
<212> TYPE: PRT
<213> ORGANISM: Artificial Sequence
<220> FEATURE:
<223> OTHER INFORMATION: Synthetic
<220> FEATURE:
<221> NAME/KEY: SUMO
<222> LOCATION: (1)..(98)
<223> OTHER INFORMATION: where the starting amino acid on the peptide
       substrate is not proline/where the amino acid following that
       sequence is not proline

<400> SEQUENCE: 35

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly

<210> SEQ ID NO 36
<211> LENGTH: 4889
<212> TYPE: DNA
<213> ORGANISM: Artificial Sequence
<220> FEATURE:
<223> OTHER INFORMATION: Synthetic

<400> SEQUENCE: 36

-continued

```
actgaccatt taaatcatac ctgacctcca tagcagaaag tcaaaagcct ccgaccggag      60
gcttttgact tgatcggcac gtaagaggtt ccaactttca ccataatgaa ataagatcac     120
taccgggcgt atttttgag ttatcgagat tttcaggagc taaggaagct aaaatgagcc     180
atattcaacg ggaaacgtct tgctcgaggc cgcgattaaa ttccaacatg gatgctgatt     240
tatatgggta taaatgggct cgcgataatg tcgggcaatc aggtgcgaca atctatcgat     300
tgtatgggaa gcccgatgcg ccagagttgt ttctgaaaca tggcaaaggt agcgttgcca     360
atgatgttac agatgagatg gtcaggctaa actggctgac ggaatttatg cctcttccga     420
ccatcaagca ttttatccgt actcctgatg atgcatggtt actcaccact gcgatcccag     480
ggaaaacagc attccaggta ttagaagaat atcctgattc aggtgaaaat attgttgatg     540
cgctggcagt gttcctgcgc cggttgcatt cgattcctgt ttgtaattgt ccttttaacg     600
gcgatcgcgt atttcgtctc gctcaggcgc aatcacgaat gaataacggt ttggttggtg     660
cgagtgattt tgatgacgag cgtaatggct ggcctgttga acaagtctgg aaagaaatgc     720
ataagctttt gccattctca ccggattcag tcgtcactca tggtgatttc tcacttgata     780
accttatttt tgacgagggg aaattaatag gttgtattga tgttggacga gtcggaatcg     840
cagaccgata ccaggatctt gccatcctat ggaactgcct cggtgagttt ctccttcat     900
tacagaaacg cttttttcaa aaatatggta ttgataatcc tgatatgaat aaattgcagt     960
ttcacttgat gctcgatgag tttttctaat gagggcccaa atgtaatcac ctggctcacc    1020
ttcgggtggg cctttctgcg ttgctggcgt ttttccatag gctccgcccc cctgacgagc    1080
atcacaaaaa tcgatgctca agtcagaggt ggcgaaaccc gacaggacta taaagatacc    1140
aggcgtttcc ccctggaagc tccctcgtgc gctctcctgt tccgaccctg ccgcttaccg    1200
gatacctgtc cgcctttctc ccttcgggaa gcgtggcgct ttctcatagc tcacgctgta    1260
ggtatctcag ttcggtgtag gtcgttcgct ccaagctggg ctgtgtgcac gaacccccg    1320
ttcagcccga ccgctgcgcc ttatccgta actatcgtct tgagtccaac ccggtaagac    1380
acgacttatc gccactggca gcagccactg gtaacaggat tagcagagcg aggtatgtag    1440
gcggtgctac agagttcttg aagtggtggc ctaactacgg ctacactaga agaacagtat    1500
ttggtatctg cgctctgctg aagccagtta cctcggaaaa agagttggta gctcttgatc    1560
cggcaaacaa accaccgctg gtagcggtgg ttttttgtt tgcaagcagc agattacgcg    1620
cagaaaaaaa ggatctcaag aagatccttt gatttctac cgaagaaagg cccacccgtg    1680
aaggtgagcc agtgagttga ttgcagtcca gttacgctgg agtctgccca ggcatcaaat    1740
aaaacgaaag gctcagtcga aagactgggc ctttcgtttt atctgttgtt tgtcggtgaa    1800
cgctctctac tagagtcaca ctggctcacc ttcgggtggg cctttctgcg tttatacaca    1860
gctaacacca cgtcgtccct atctgctgcc ctaggtctat gagtggttgc tggataacgt    1920
gcgtaattgt gctgatctct tatatagctg ctctcattat ctctctaccc tgaagtgact    1980
ctctcacctg taaaaataat atctcacagg cttaatagtt tcttaataca aagcctgtaa    2040
aacgtcagga taacttctat attcagggag accacaacgg tttccctcta caaataattt    2100
tgtttaactt taaagaggag aaatactaga gtgtcggacag tgaagtcaac caggaagcga    2160
aaccggaagt gaaaccggaa gtcaaacctg aaacgcacat taatctgaaa gtcagcgatg    2220
gttccagtga atcttcttc aaaattaaaa aaactacgcc gttacgtcgt ttgatggaag    2280
catttgcgaa acgccaggc aaggaaatgg attccctccg cttcttatat gacgggattc    2340
gtatccaagc agaccaaacc ccggaagatc tggacatgga agacaacgat attattgaag    2400
```

-continued

| | | | | |
|---|---|---|---|---|
| cacatcgcga | acagattggg | ggcgggaacg | cagcatctgc | gcgccgcgaa aatctctatt | 2460 |
| ttcagggcat | gtccccgatc | ctgggttact | ggaaaatcaa | agggttagtg cagccaaccc | 2520 |
| gtctgttatt | agaatacctg | gaggaaaaat | acgaggaaca | cctgtacgag cgcgatgaag | 2580 |
| gcgataaatg | gcgcaataaa | aaattcgaac | tcgggctgga | attcccaaac ttaccctatt | 2640 |
| atattgatgg | agatgttaaa | ttgacccagt | ctatggcaat | cattcgctat attgcagata | 2700 |
| aacataacat | gttgggcggc | tgtcctaagg | agcgcgcgga | aattagtatg ctggaaggcg | 2760 |
| cggtgctgga | tatccgctat | ggtgttagcc | gcattgcgta | ctcgaaagat tttgagacgc | 2820 |
| tcaaagttga | ttttctgagt | aaactgcctg | aaatgttaaa | gatgtttgaa gatcgcttgt | 2880 |
| gtcacaaaac | gtatttaaat | ggtgatcatg | tcacccatcc | agactttatg ctgtatgatg | 2940 |
| cgcttgatgt | ggttttgtac | atggatccga | tgtgcctgga | tgccttccg aagctggtct | 3000 |
| gtttcaaaaa | acgcatcgag | gctattccgc | aaatcgacaa | atatctcaaa tctagtaaat | 3060 |
| acatcgcgtg | gcctctgcag | ggctggcaag | cgacctttgg | tggggcgat catccgccaa | 3120 |
| aatgataatc | gcgcaaaaaa | ccccgcttcg | gcggggtttt | tcgcacgtc tccatcgctt | 3180 |
| gcccaagttg | tgaagcacag | ctaacaccac | gtcgtcccta | tctgctgccc taggtctatg | 3240 |
| agtggttgct | ggataacgcc | acggaaatca | ataacctgaa | gatatgtgcg acgagctttt | 3300 |
| cataaatctg | tcataaatct | gacgcataat | gacgtcgcat | taatgatcgc aacctattta | 3360 |
| ttatattcag | ggagaccaca | acggtttccc | tctacaaata | attttgttta actttgcttc | 3420 |
| aatctaaatt | agtaaggagg | tagtcaatga | caaatcctgg | tgtaagtgcc tgcaagtta | 3480 |
| ataccgcata | taccgctggg | cagttagtca | cttataacgg | caagacctac aagtgcttgc | 3540 |
| agcctcacac | atccttggca | ggttgggaac | cgtccaatgt | acccgccctt tggcaacttc | 3600 |
| agggctctgc | cggtagtgcg | gcgggttccg | gtgaatttaa | ctcgttgcct gctgagcgta | 3660 |
| tccaagaaat | tcagaaggca | attgaactgt | ttagcgtggg | tcaaggccca gccaaaacga | 3720 |
| tggaggaagc | gagcaaacgt | tcgtatcagt | tctgggatac | gcaaccggtg ccgaagctcg | 3780 |
| gtgaagtggt | gaatacgcac | gggcctgttg | agccggataa | ggacaatatt cgtcaggagc | 3840 |
| catatacgct | gcctcagggt | ttcacttggg | acgccctgga | cctgggtgac cgtggtgtgc | 3900 |
| tgaaagaact | gtacaccctg | cttaatgaga | attatgtaga | agatgacgac aacatgttcc | 3960 |
| gttttgacta | tagcccggaa | ttcctgttat | gggcactccg | tccgccgggt tggctgccgc | 4020 |
| agtggcattg | cggtgtccgc | gtagtttcga | gccgtaaact | cgtaggtttc atcagtgcaa | 4080 |
| tcccggccaa | cattcatatc | tatgacaccg | agaaaaaaat | ggtagaaatt aacttcctgt | 4140 |
| gtgttcataa | gaagttgcgt | agcaaacgcg | tagcgcctgt | cctcattcgt gaaatcacgc | 4200 |
| gccgcgtaca | tttagaaggt | atcttccagg | cagtatatac | tgctggcgtc gtgctcccaa | 4260 |
| aaccggttgg | gacttgccgc | tattggcacc | gctctctgaa | tccgcgtaag ctgattgaag | 4320 |
| ttaaatttag | ccatttgtca | cgcaacatga | ccatgcagcg | caccatgaaa ctttaccgtc | 4380 |
| tgccggaaac | cccgaaaact | gctggtttgc | gcccaatgga | gacgaaagat attcctgtcg | 4440 |
| tccatcagct | gctgacgcgt | tatttaaaac | agtttcactt | aactcctgtc atgagccagg | 4500 |
| aagaggttga | acattggttt | tatccgcaag | aaaacatcat | cgacaccttc gtagtggaga | 4560 |
| atgcgaatgg | cgaagtcacg | gactttttat | ccttctatac | tttgccgagc accatcatga | 4620 |
| accatccgac | cctaaaaagc | ctgaaggccg | cgtactcatt | ttataatgtc cacacgcaga | 4680 |
| ccccgttatt | ggatctgatg | tctgatgcgt | tggtcctggc | caaaatgaaa ggtttcgacg | 4740 |

-continued

```
tttttaatgc gctggacctg atggagaaca aaacctttct ggaaaaattg aaattcggaa    4800
ttggcgatgg taatctgcaa tactatctgt ataattggaa atgcccgtcg atgggtgcgg    4860
aaaaagttgg tctggtactg cagtagtaa                                      4889
```

<210> SEQ ID NO 37
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: exemplary human-myristoyl transferase-1 recognition
      substrate
<222> LOCATION: (1)..(8)
<223> OTHER INFORMATION: peptides with the sequence X1X2X3X4X5X6X7X8
      where X1 is glycine, X2 and X5 are small uncharged residues, but
      proline; X6 is any residue but proline and X3, X4, X7 and X8 are
      any residues

<400> SEQUENCE: 37

Gly Asn Ala Ala Ala Ala Arg Arg
1               5